United States Patent [19]

Mitchell

[11] Patent Number: 4,461,725

[45] Date of Patent: Jul. 24, 1984

[54] PROTEIN COMPOUNDS

[76] Inventor: David C. Mitchell, 2472 S. 900 East, #8, Salt Lake City, Utah 84106

[21] Appl. No.: 392,371

[22] Filed: Jun. 25, 1982

Related U.S. Application Data

[63] Continuation-in-part of Ser. No. 194,626, Oct. 6, 1980, abandoned.

[51] Int. Cl.³ .................. C07C 103/52; C07G 7/00; A61K 35/14; A61K 37/00
[52] U.S. Cl. ..................... 260/112.5 R; 260/112 R; 424/101; 424/177
[58] Field of Search ............ 260/121, 112.5 R, 112 R; 424/101, 177

[56] References Cited

U.S. PATENT DOCUMENTS 2,803,584  8/1957  Hodge et al. .................... 167/65

OTHER PUBLICATIONS

Herbert M. Gross et al., "Bacitracin III, Formulatory Characteristics of Zinc Bacitracin," 45 Journal of the American Pharmaceutical Association 447-449 (1956).
Herbert S. Anker et al., "Bacitracin: Methods of Production, Concentration, and Partial Purification, with a Summary of the Chemical Properties of Crude Bacitracin," 55 Journal of Bacteriology 249-255 (1948).
Chem. Abstr., vol. 95, (1981), 162301n.
Chem. Abstr., vol. 95, (1981), 126633p.
Chem. Abstr., vol. 87, (1977), 150331u.
Chem. Abstr., vol. 79, (1973), 133765f.
Chem. Abstr., vol. 88, (1978), 119588e.
Chem. Abstr., vol. 84, (1976), 175472s.
Chem. Abstr., vol. 77, (1972), 150400j.
Chem. Abstr., vol. 85, (1976), 143521m.
Chem. Abstr., vol. 85, (1976), 175582y.
Chem. Abstr., vol. 73, (1970), 73065s.
Biol. Abstr., 72, 40787.
Chem. Abstr., vol. 69, (1968), 51037z.
Chem. Abstr., vol. 67, (1967), 17843h.
Chem. Abstr., vol. 96, (1982), 17745b.
Chem. Abstr., vol. 95, (1981), 18928e.

Primary Examiner—Delbert R. Phillips
Attorney, Agent, or Firm—H. Ross Workman; Allen R. Jensen; Dale E. Hulse

[57] ABSTRACT

The present invention is directed to certain multiprotein compounds and methods for using such compounds in the treatment of psoriasis, arthritis, erythropoietic protoporphyria, and scar tissue and wounds. These multiprotein compounds include beta-lactoglobulin, alpha-lactalbumin, and bacitracin. The beta-lactoglobulin proteins are linked to alpha-lactalbumin proteins by a plurality of organic linkages formed by reacting various alcohols, e.g., noncyclic alcohols, steroid alcohols, triterpenoid alcohols, and thioglycerol therewith. The alpha-lactalbumin proteins are linked to the bacitracin proteins by a plurality of organic linkages formed by reacting with fatty acids therewith. A selenium ion may be bonded to each bacitracin protein molecule of the multiprotein compounds. Additionally, pairs of bacitracin molecules may be linked by zinc ions or other cations, to form a salt with the bacitracin.

29 Claims, 9 Drawing Figures

U.S. Patent Jul. 24, 1984 Sheet 1 of 2 4,461,725
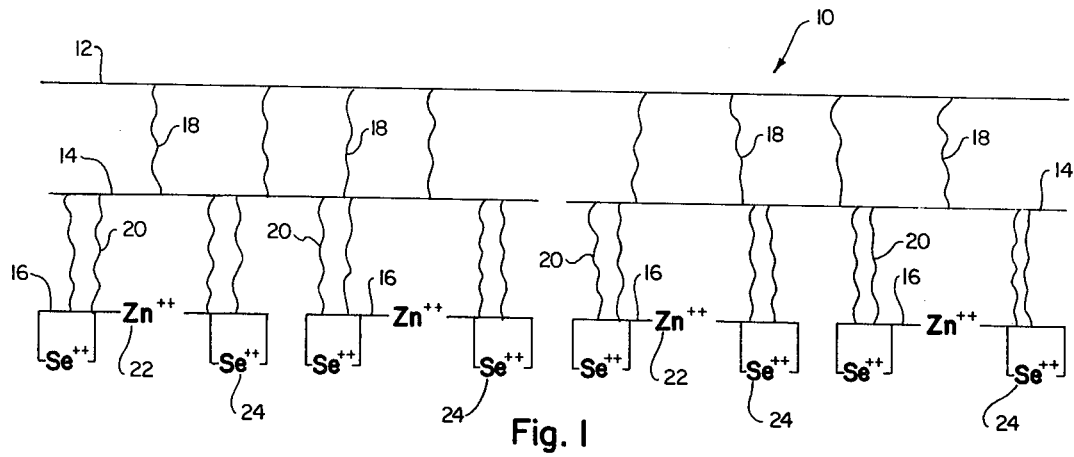
Fig. 1
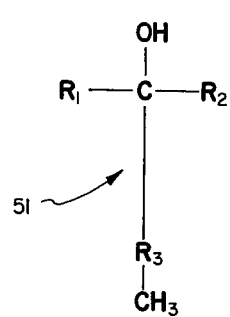
Fig. 3A
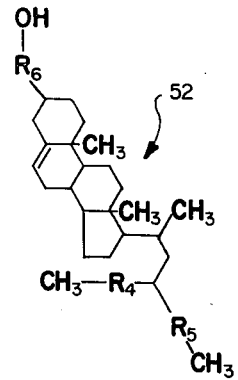
Fig. 3B
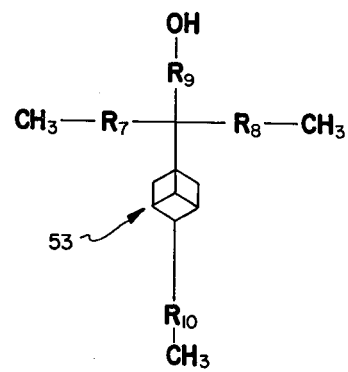
Fig. 3C
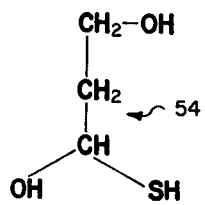
Fig. 3D
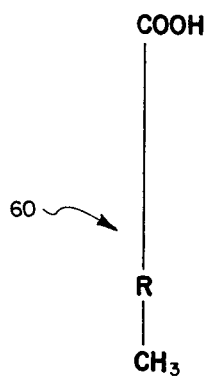
Fig. 4
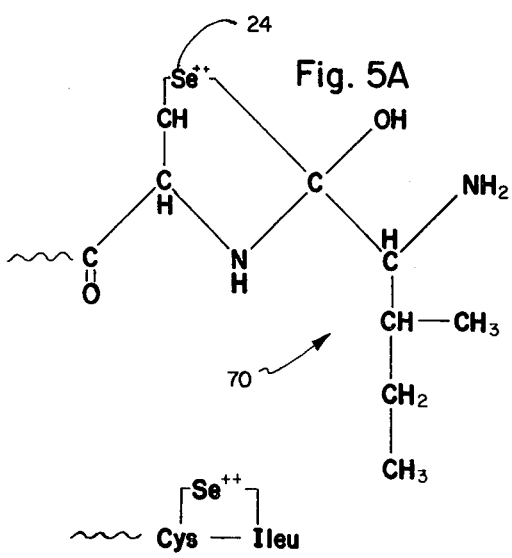
Fig. 5A
Fig. 5

PROTEIN COMPOUNDS

RELATED APPLICATIONS

This application is a continuation-in-part of my co-pending U.S. patent application Ser. No. 194,626, filed Oct. 6, 1980, (now abandoned) entitled "MATREX," which is incorporated herein by reference.

BACKGROUND

Field of the Invention

The present invention relates to multiprotein compounds which are particularly useful in the treatment of such medical disorders as psoriasis, arthritis, erythropoietic protoporphyria, and scar tissue and wounds.

The Prior Art

A. Psoriasis

Psoriasis is a skin disease which is typically characterized by white or red scaly patches of skin at practically any body location. Ulcerations of the skin and bleeding may also, but not necessarily, be experienced by some victims of psoriasis. In extremely severe cases, blood transfusions may even be necessary. It is estimated that one to three percent (1-3%) of the world population suffers from psoriasis.

Simply stated, psoriasis may be defined as an acute overproliferation of corneocytes (white skin cells). Typical psoriasis treatments have thus attempted to impede the proliferation of corneocytes and to allow the skin layers to heal themselves. Typical treatments include the following categories of medicants: (1) anti-infectives, (2) cleansing agents and detergents, (3) enzyme preparations, (4) preparations containing tar, allantoin, or anthralin, and (5) preparations containing vitamins and nutrients.

The anti-infective treatments contain such active ingredients as fluocinolone acetonide, neomycin, and p-chloro-m-xylenol, generally either in a detergent base or in an oil-water emulsion. It has been found, however, that these treatments provide limited active absorption into the skin, and are extremely limited in their anti-proliferative action against the corneocytes.

Cleansing agents and detergents are useful for washing away dead skin cells; however, these are not particularly useful in stopping proliferation of the corneocytes.

Typical enzyme preparations include such ingredients as pancreatin and pyridoxine hydrochloride. These preparations are generally taken orally and attempt to disrupt the enzymatic reactions which occur during the proliferative cycles of the corneocytes. However, in reality, these preparations achieve only minimal disruption of the proliferative cycles and are often absorbed or destroyed, in large part, before reaching the corneocytes.

A typical hormone and steroid treatment of psoriasis is the injection of corticotrophin. Since many of the anti-infective treatments involve cortico-steroids, many of the same problems associated with anti-infective treatments are also characteristic of the hormone steroid treatments.

The preparations containing tar, allantoin and anthralin are generally applied topically. The action of these preparations in slowing the proliferation of corneocytes has been found to be limited. Moreover, these preparations can result in many undesirable effects, e.g., skin cancer, organ cancer, an increase in the aging process, conjunctivitis, corneal opacity of the eyes, renal and skin irritation, postular folliculitis, cutaneous sensitization of the skin or scalp, poly-metastatitis, metastatic carcinoma, partial or total blindness, and damage to or failure of the liver, bladder, or kidneys.

A typical vitamin and nutrient treatment includes as an active ingredient, 13-cis-retenoic acid (modified vitamin A). However, the activity of such a preparation in treating psoriasis has been found to be extremely limited.

From the foregoing, it will be appreciated that what is needed in the art is a psoriasis treatment which can be readily absorbed by the skin and which is effective in stopping the proliferation of corneocytes, without exhibiting adverse side effects. Such a compound and treatment are disclosed and claimed herein.

B. Arthritis

Arthritis may be defined as an acute inflammation of the joints, generally accompanied by significant swelling and pain. In some arthritis victims, calcification of the joints and partial or total immobilization thereof may also occur. Arthritis is a well-known malady; indeed, it is estimated that every thirty-three (33) seconds, another American is afflicted with arthritis. Arthritis is generally believed to be caused by the polymerization of collagen in the joints.

Typical preparations for the treatment of arthritis have included the following, and combinations thereof: (1) adenosine preparations, (2) anabolic agents, (3) analgesics, (4) anesthetics, (5) enzymes, (6) hormones and steroids, (7) hypnotics and tranquilizers, (8) muscle relaxants, (9) narcotics, and (10) phenylbutazones. These drugs, however, have been found to be extremely limited in their action of breaking up the polymerized collagen which causes arthritis and are generally directed more toward temporarily relieving the symptoms of arthritis such as arthritic pain. Moreover, these drugs are accompanied by numerous undesirable side effects.

Some of the side effects experienced with the use of the adenosine preparations include flushing of the skin and face, restlessness, hypertension, dizziness, dyspnea, epigastric discomfort, nausea, erythema, and diuresis.

Side effects associated with the anabolic agents include deepening of the voice (in women), sterility (primarily in men and children), carcinoma of the prostate gland, arteriosclerosis, hypertensive heart disease, periodic paralysis, and many of the side effects previously listed for the cancer hormone and steroid treatments.

Side effects sometimes associated with the analgesics include nausea, vomiting, intestinal irritation, bleeding of the stomach, thinning of the blood, kidney damage, and addiction. Gastrointestinal upset is also a common side effect experienced with the use of the enzyme preparations. The side effects experienced with the arthritis hormone and steroid preparations are similar to those experienced with the hormone and steroid preparations for the treatment of cancer. Side effects associated with hypnotics and tranquilizers include the well-known toxicities of barbiturates, hypersensitivity, and addiction.

Those side effects associated with the muscle relaxants include delerium, confusion, constipation, depression, hiccups, hypoactivity, hypertension, headaches, nausea, salivation, skin rash, slurried speech, tremors, urine retention, urticaria, hallucinations, muscle spasms, insomina, rage, jaundice, and addiction. The narcotic preparations also have undesirable side effects, including gastrointestinal problems, headaches, and addiction, while those associated with the phenylbutazone preparations include fever, sore throats, lesions of the mouth, intestinal hemorrhaging, skin reactions, and an increase in weight.

It will thus be appreciated that what is needed in the art is an effective treatment for arthritis which effectively breaks up polymerized collagen, which prevents further polymerization of collagen, and which is not accompanied by undesirable side effects. Such a compound and treatment are disclosed and claimed herein.

C. Erythropoietic Protoporphyria

Erythropoietic protoporphyria is a disease which effects one in about every 100,000 persons. It is characterized by a concentration of porphyrin IX in the urine, and often by swelling, discoloration, and splitting of the skin. Porphyrin IX, a precursor of hemoglobin, accumulates in the victims of this disease when the liver and red bone marrow fail to properly manufacture hemoglobin.

Porphyrin IX reacts with the cell wall so as to cause an accumulation of porphyrin just below the cell membrane, thus resulting in the swelling, discoloration, and splitting of the skin cells. Erythropoietic protoporphyria may also be characterized by other symptoms such as brain disfunctions, individual idiosyncrasies, liver and kidney damage, ruptured veins and arteries, hemorrhaging at various body locations, and even mental retardation in severe cases.

No compound or method exists in the prior art for curing or even effectively treating erythropoietic protoporphyria. It would, therefore, be a significant advancement in the art to provide an effective treatment for erythropoietic protoporphyria. Such a compound and treatment are disclosed and claimed herein.

D. Scar Tissue and Wounds

Typical prior art preparations for treating scar tissue and wounds include: (1) anti-infectives, (2) enzymes and antioxidants, (3) hormones and steroids, and (4) tissue stimulants. Most of these treatments have undesirable side effects and are usually not effective in promoting actual tissue regeneration.

The anti-infective preparations attempt to reduce bacterial infection, thereby promoting wound healing. These preparations do little, if anything, to actually activate the tissue regeneration mechanisms of the body. Moreover, side effects such as skin irritations or sensitization reactions may be experienced during the use of such preparations.

The enzyme and antioxidant preparations were developed with the goal of actually activating the healing mechanisms of the body, thereby promoting tissue regeneration. However, in reality, their activity in promoting tissue regeneration is extremely limited, if not nonexistant. Moreover, adverse side effects such as hemopillia, allergic reactions, nausea, vomiting, diarrhea, skin rash, and urticaria may be experienced with the use of such preparations.

The hormone and steroid preparations have a certain amount of anti-inflammatory action and attempt to provide the scar tissue and wounds with some of the new materials needed in the construction of new cellular tissue. These preparations, however, only provide a few of the needed raw materials and have many adverse side effects which are discussed hereinabove in connection with the hormone and steroid treatments used for cancer.

The tissue stimulant preparations are usually applied topically as biological cleansers and contain proteins, amino acids, and/or vitamins which are needed for repairing cellular breaks in the tissues. Although these preparations provide some of the raw materials for building new tissue, they do not provide all the necessary raw materials and do not in themselves promote tissue regeneration.

From the foregoing, it will be appreciated that it would be a significant advancement in the art to provide a treatment for scar tissue and wounds which has anti-bacterial activity; supplies most, if not all, of the raw materials necessary to promote wound healing; promotes actual tissue regeneration; and yet does not have any adverse side effects. Such a compound and treatment are disclosed and claimed herein.

BRIEF SUMMARY AND OBJECTS OF THE INVENTION

The present invention relates to multiprotein chemical compounds and methods for treating cancer, psoriasis, arthritis, erythropoietic protoporphyria, and scar tissue and wounds. The various chemical compounds used in these treatments are substantially similar and include beta-lactoglobulin, alpha-lactalbumin, and bacitracin. The alpha-lactalbumin molecules are linked to the beta-lactoglobulin molecules by a plurality of organic linkages which are formed by reacting alcohols therewith; the alcohols are selected from the group consisting of noncyclic aliphatic alcohols, steroid alcohols, and triterpenoid alcohols. Additionally, thioglycerol molecules may be reacted with the beta-lactoglobulin molecules and the alpha-lactalbumin molecules to provide further organic linkages therebetween, thus providing additional strength and stability to the overall chemical structure. The bacitracin molecules are linked to the alpha-lactalbumin molecules by a plurality of organic linkages which are formed by reacting fatty acids therewith. Additionally, the compounds further include selenium ions, each ion having a $+2$ charge. Each selenium ion is substituted for a sulfur atom in a sulfide bond between adjacent isoleucine and cysteine amino acid residues in a corresponding bacitracin molecule. Optionally, compounds within the scope of the present invention may further include four zinc ions, each ion having a $+2$ charge and being associated with two bacitracin molecules so as to form a zinc salt therewith.

In the treatment of the medical disorders discussed above, the multiprotein compounds of the present invention may be applied either topically or surgically, as in needed. Significantly, the multiprotein compounds of the present invention have not been found to have adverse side effects, and yet have exhibited: (1) antimitotic activity in stopping the proliferation of cancerous cells without harming healthy cells, (2) the ability to be readily absorbed by skin afflicted with psoriasis and to stop proliferation of corneocytes, (3) activity in breaking up polymerized collagen and in preventing further polymerization of collagen for the effective treatment of arthritis, (4) activity in the effective treatment of erythropoietic protoporphyria, and (5) activity in the effective treatment of scar tissue and in the promotion of wound healing and tissue regeneration.

It is, therefore, an object of the present invention to provide novel multiprotein compounds which include beta-lactoglobulin, alpha-lactalbumin, and bacitracin.

It is another object of the present invention to provide a novel seleno-bacitracin compound which is made from bacitracin and selenium ions, each selenium ion being substituted for a sulfur atom in a sulfide bond between adjacent isoleucine and cysteine amino acid residues in a corresponding bacitracin molecule.

Still another object of the present invention is to provide an effective method for prohibiting the replication of deoxyribonucleic acid in cells, thereby prohibiting mitosis.

Yet another object of the present invention is to provide an effective method for treating psoriasis by stopping proliferation of corneocytes.

A further object of the present invention is to provide an effective method for treating arthritis.

Still another object of the present invention is to provide an effective method for treating erythropoietic protoporphyria.

Yet another object of the present invention is to provide an effective method for treating scar tissue and for promoting wound healing and tissue regeneration.

These and other objects and features of the present invention will become more fully apparent from the following description and appended claims, taken in conjunction with the accompanying drawings.

BRIEF DESCRIPTION OF THE DRAWINGS

FIG. 1 is a representative schematic illustration of the novel compounds of the present invention.

FIGS. 3 A-D illustrate the various alcohols which are used to link beta-lactoglobulin molecules to alpha-lactalbumin molecules in the compounds of the present invention. In particular, FIG. 3A illustrates a noncyclic aliphatic alcohol molecule; FIG. 3B illustrates a steroid alcohol molecule; FIG. 3C illustrates a triterpenoid alcohol molecule; and FIG. 3D illustrates a thioglycerol molecule.

FIG. 4 illustrates the fatty acids which are used to link alpha-lactalbumin molecules to bacitracin molecules in the compounds of the present invention.

FIGS. 5 and 5A illustrate the manner of bonding of each selenium ion to a corresponding bacitracin molecule in the compounds of the present invention. FIG. 5 illustrates generally the selenium bridge between adjacent cysteine and isoleucine amino acid residues of the bacitracin molecule; FIG. 5A contains a more detailed illustration and shows the molecular structure of the cysteine and isoleucine amino acid residues.

DETAILED DESCRIPTION OF A PREFERRED EMBODIMENT OF THE PRESENT INVENTION

Figure 2:
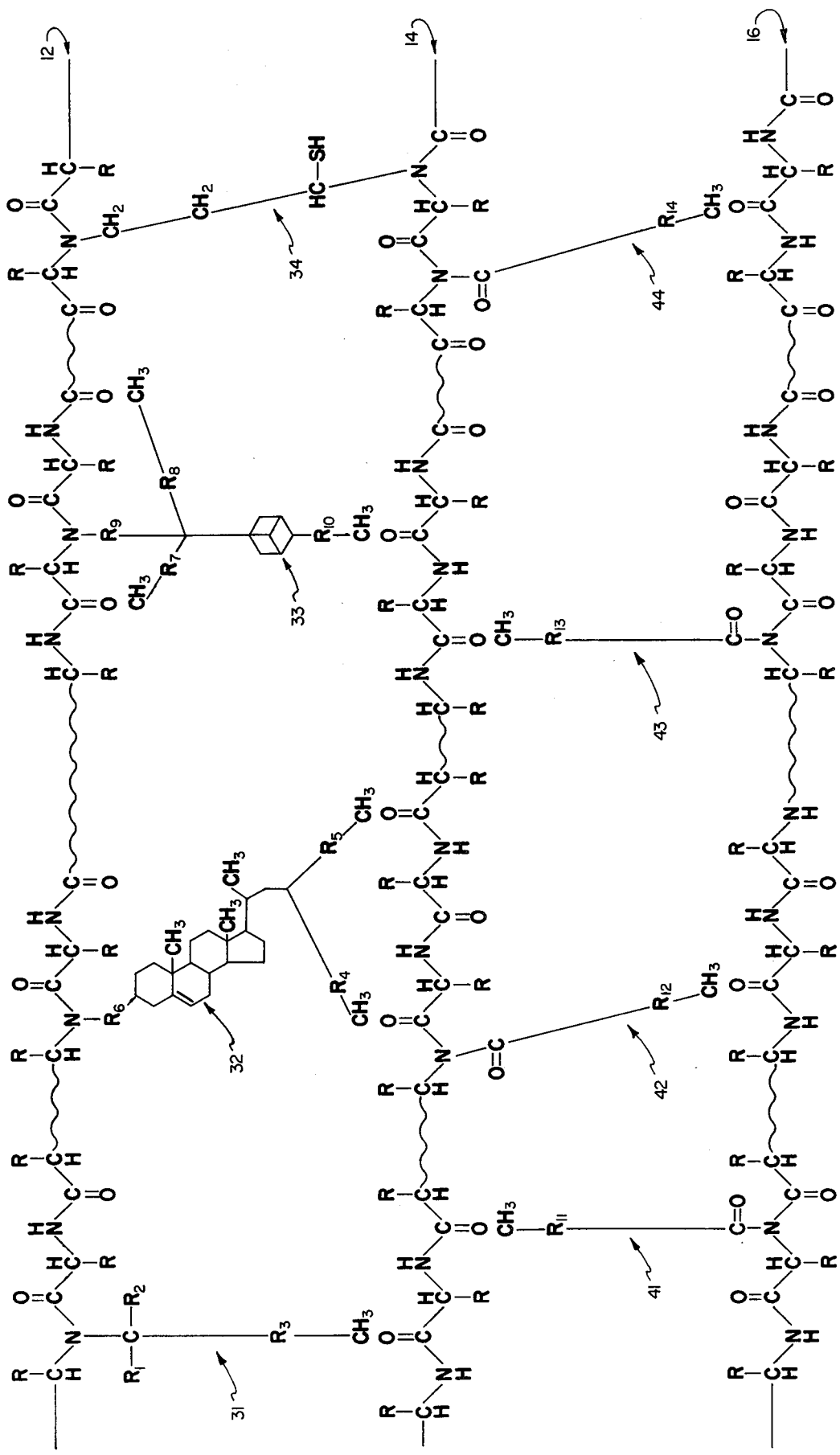
FIG. 2 is a schematic illustration of the manner in which beta-lactoglobulin molecules are linked to alpha-lactalbumin molecules in the compounds of the present invention, and the manner in which alpha-lactalbumin molecules are linked to bacitracin molecules.

2. Compounds of Present Invention and Methods of Manufacture

Reference is now made to the drawings wherein like parts are represented with like numerals throughout. The present invention relates to multiprotein compounds and methods for treating psoriasis, arthritis, erythropoietic protoporphyria, and scar tissue and wounds. The various chemical compounds used in these treatments are substantially similar and are generically represented by the multiprotein compound, generally designated 10, in FIG. 1.

As discussed in greater detail hereinafter, the multiprotein compounds of the present invention include a variety of compounds having various combinations of beta-lactoglobulin proteins, alpha-lactalbumin proteins, and bacitracin proteins. However, for purposes of understanding these multiprotein compounds, the following discussion is in terms of a presently preferred species of these compounds.

With particular reference to FIG. 1, multiprotein compound 10 comprises one molecule of beta-lactoglobulin 12, two molecules of alpha-lactalbumin 14, and eight molecules of bacitracin 16. The alpha-lactalbumin molecules 14 are linked to the beta-lactoglobulin molecule 12 by a plurality of organic linkages 18. The bacitracin molecules 16 are linked to the alpha-lactalbumin molecules 14 by a plurality of organic linkages 20. Multiprotein compound 10 preferably further comprises eight selenium ions 24 (each having a +2 charge). Additionally, multiprotein compound 10 may optionally include, four zinc ions 22 (each having a +2 charge); when such zinc ions are present, each zinc ion 22 is associated with two bacitracin molecules 16 so as to form a zinc salt therewith.

The various organic linkages between the proteins 12, 14, and 16 of multiprotein compound 10 are best illustrated in FIG. 2. Alpha-lactalbumin molecules 14 are linked to beta-lactoglobulin molecule 12 by reacting the proteins with various alcohols to provide linkages 31-34; examples of the alcohols are illustrated in FIGS. 3A-D. Thus, organic linkages 31-34 correspond to the organic linkages generally represented as 18 in FIG. 1.

Still referring to FIG. 2, bacitracin molecules 16 are linked to alpha-lactalbumin molecules 14 by reacting the proteins with fatty acids (illustrated in FIG. 4) to form organic linkages 41-44. Thus, organic linkages 41-44 of FIG. 2 correspond to the organic linkages generally represented as 20 in FIG. 1.

Initially, it should be recognized that the representation of each of proteins 12, 14, and 16 in FIG. 2 is general in nature, and there has been no attempt to identify the individual amino acids in the long polypeptide chains of proteins 12, 14, and 16. The R groups shown in each of these polypeptide chains would, of course, correspond to those R groups actually present in the well-known sequence of amino acids for each of these proteins. The wavy lines used in the illustration of proteins 12, 14, and 16 in FIG. 2 simply represent continuations in the well-known polypeptide chains. The straight lines at the end of each of proteins 12, 14 and 16 in FIG. 2 simply represent the ends of each polypeptide chain. Finally, it should be noted that the two-dimensional representations of the proteins and organic linkages in both FIGS. 1 and 2 are used for sake of clarity. In reality, these proteins and linkages assume complex three-dimensional configurations, but no attempt has been made to illustrate any such three-dimensional configuration.

Referring now to FIGS. 2 and 3A-D, it will be seen that a variety of alcohols may be used to form organic linkages 31-34 between beta-lactoglobulin protein 12 and alpha-lactalbumin proteins 14. Such alcohols include noncyclic aliphatic alcohols, steroid alcohols, triterpenoid alcohols, and thioglycerol. It will be recognized that the arrangement of organic linkages 31-34 of FIG. 2 is given by way of illustration only, and is not intended to represent the order or frequency of the different types of linkages as they may actually appear in multiprotein compound 10.

FIG. 3A shows a noncyclic aliphatic alcohol, generally designated 51, which reacts with proteins 12 and 14 to form organic linkage 31 of FIG. 2. As seen in FIG. 3A, noncyclic aliphatic alcohol 51 has three radical groups (hereinafter referred to as "R" groups). $R_1$ and $R_2$ may be hydrogen or any organic side chain which will not create steric hindrance problems and which is nontoxic when substituted in multiprotein compound 10. It has been found that $R_1$ and $R_2$ should preferably not be longer than about 50 carbon atoms in length, because steric hindrance becomes a substantial obstacle with such longer side chains. $R_3$ can be any organic constituent having a chain of carbon atoms from about 6 to about 48 atoms in length such that the overall length of noncyclic aliphatic alcohol 51 is from about 8 to about 50 carbon atoms in length. Presently, the most preferred length for the carbon chain of alcohol 51 and thus for organic linkage 31 is from about 14 to about 20 carbon atoms long.

In the reaction of noncyclic aliphatic alcohol 51 with proteins 12 and 14 to form organic linkage 31, the hydroxyl group of alcohol 51 reacts with an amino group on protein 12, thereby forming a water molecule in a condensation reaction so as to result in a carbon-to-nitrogen bond. The methyl group of alcohol 51 holds a slightly positive electrical charge, and is thus electrostatically attracted and "bonded" to a corresponding negatively charged carbonyl group on protein 14.

Conversely, it will be appreciated that the hydroxyl group of alcohol 51 may react with an amino group of protein 14 and the methyl group of alcohol 51 may associate with a carbonyl group of protein 12 to form a similar linkage (not shown). The preference of one way or the other is influenced by such factors as steric hindrance and temperature. The probability of binding alcohols 51 (as well as alcohols 52-54) in a given orientation depends in large part upon the velocity of the alcohol molecules, which in turn depends on the thermal energy present (temperature) and on the size of the alcohol molecules (steric hindrance). Moreover, as the length of the alcohol molecule increases, the probability of that molecule forming a bond between proteins 14 and 20 decreases since a longer molecule will have a slower velocity and thus less chance of forming a bond upon collision. Alcohols with carbon chains between about 14 and about 20 carbons have adequate length for bonding proteins 12 and 14, and steric hindrance at this length is not a significant bond-prohibiting factor.

As seen in FIG. 3B, a steroid alcohol, generally designated 52, may be used to form organic linkage 32 of FIG. 2. Steroid alcohol 52 may be any alcohol having the general configuration shown in FIG. 3B, including three possible R groups ($R_4$, $R_5$, and $R_6$) which comprise any number of carbon atoms such that the overall length of the longest carbon chain in steroid alcohol 52 is from about 8 to about 50 carbon atoms in length. Certain of the other $R_4$, $R_5$, or $R_6$ may not be required if the length of the other R groups is sufficient to provide the indicated length. Again, the preferred length for alcohol 52 is from about 14 to about 20 carbon atoms long because, as previously discussed herein, alcohols 52 which are longer than 20 carbon atoms become increasingly difficult to bind to proteins 12 and 14 due to steric hindrance and the lower probability of attaining the collision velocity needed for binding.

Steroid alcohol 52 reacts with proteins 12 and 14 much in the same way as noncyclic aliphatic alcohol 51. As best illustrated in FIG. 2, the hydroxyl group of steroid alcohol 52 reacts with an amino group of protein 12, thereby forming a water molecule in a condensation reaction so as to result in a carbon-to-nitrogen bond. Similarly, each of the two terminal methyl groups of steroid alcohol 52 associate with a corresponding carbonyl group of protein 14 by electrostatic attraction. As with alcohol 51, alcohol 52 may also serve to link proteins 12 and 14 by reacting with an amino group of protein 14 and associating its methyl groups with the carbonyl groups of protein 12 to form a linkage (not shown) having an orientation inverse to that of linkage 32.

As seen in FIG. 3C, a triterpenoid alcohol, generally designated 53, may be reacted with proteins 12 and 14 to form linkage 33 shown in FIG. 2. Triterpenoid alcohol 53 may be any alcohol having the general configuration shown in FIG. 3C, including four R groups $R_7$, $R_8$, $R_9$, and $R_{10}$. The hydroxyl group of triterpenoid alcohol 53 reacts through a condensation reaction with an amino group of protein 12, as heretofore explained, to form a carbon-to-nitrogen bond. The methyl group attached to $R_{10}$ of alcohol 53 associates with a carbonyl group of protein 14 in an electrostatic "bond" as heretofore explained. Moreover, the two methyl groups attached to $R_7$ and $R_8$ may, but need not necessarily, associate electrostatically with carbonyl groups of protein 12.

$R_9$ and $R_{10}$ of triterpenoid alcohol 53 should be of such length to provide an overall carbon chain of from about 8 to about 50 carbon atoms long, with the presently most preferred range being from about 14 to about 20 carbon atoms long. Of course, this length could be provided entirely by either $R_9$ or $R_{10}$, thereby eliminating the necessity of the other R group. Alternatively, $R_7$ and $R_8$ may be of sufficient length (typically from about 1 to about 50 carbon atoms long) to allow for association of the methyl groups attached thereto with carbonyl groups of protein 12, as shown in FIG. 2, or may be hydrogen and thus exhibit no such association. As with alcohols 51 and 52, triterpenoid alcohol 53 may be reacted with proteins 12 and 14 in an orientation inverse to that shown by linkage 33 in FIG. 2.

Due to the three-dimensional configuration of proteins 12 and 14, it is possible, and often desirable, to provide relatively shorter organic linkages between proteins 12 and 14 at those locations where the proteins are closest to each other. Such linkages can be provided by reacting thioglycerol molecules with proteins 12 and 14, one such thioglycerol molecule 54 being illustrated in FIG. 3D. As best seen in FIG. 2, the two hydroxyl groups of thioglycerol molecule 54 react with amino groups on both proteins 12 and 14, in condensation reactions, to form linkage 34.

It will be appreciated that any combination of noncyclic aliphatic alcohols 51, steroid alcohols 52, and triterpenoid alcohols 53 may be used to form linkages 18 shown in FIG. 1. The illustration in FIG. 2 is given only to show the manner in which these alcohols bond to proteins 12 and 14, not to suggest the sequence or relative quantities of each type of organic linkage formed thereby. Moreover, it should be understood that the organic linkages formed by reacting thioglycerol molecules 54 with proteins 12 and 14 are not essential, but contribute significantly to the overall stability of the multiprotein structure.

It will also be appreciated that the important chemical groups which alcohols 51–54 need are the hydroxyl group and the methyl group which react to form linkages 31-34 as described herein. In fact, it has been found that fatty acids may also be used to form linkages 31-34. Since the carboxyl group of a fatty acid consists of a carbonyl group and a hydroxyl group, fatty acids also have the necessary chemical groups to form linkages 31-34.

It should be noted that where both alcohols and fatty acids are available to form organic linkages 31-34, the formation of linkages with the alcohols is chemically preferred over linkages with the fatty acids since the carbonyl portion of the fatty acid carboxyl groups tends to decrease the probability that a bond will be formed between proteins 12 and 14.

As discussed hereinabove, each of organic linkages 31-34 in FIG. 2 (linkages 18 in FIG. 1) are from about 8 to about 50 carbons in length, with the presently preferred range being from about 14 to about 20 carbon atoms in length. It has been found that these linkages must generally be at least about 8 carbon atoms long in order to be of sufficient length to be structurally capable of linking beta-lactoglobulin proteins 12 and alpha-lactalbumin proteins 14. However, it should be recognized that the three-dimensional configuration of certain compounds occasionally allows for shorter linkages, such as the thioglycerol linkages 34.

The maximum length for each of linkages 31-34 is controlled in large part by the desired stability of multiprotein compound 10. As the length of these linkages approaches 50 carbon atoms in length, it has been found that multiprotein compound 10 becomes increasingly less stable, thereby yielding a compound with a shortened lifetime. Compounds formed by using linkages in excess of about 50 carbon atoms in length are possible, but are generally too unstable to be practical or viable. The presently preferred length of about 14 to about 20 carbon atoms for linkages 31-34 yields multiprotein compounds 10 which are both stable and provide adequate support linkages between beta-lactoglobulin proteins 12 and alpha-lactalbumin proteins 14.

Referring now to FIGS. 2 and 4, organic linkages 41-44 are formed by reacting fatty acids, generally designated 60 in the general representation of FIG. 4, with alpha-lactalbumin molecules 14 and bacitracin molecules 16. The carboxyl group of each fatty acid 60 reacts with an amino group of either protein 14 or protein 16, thereby forming a water molecule and resulting in an amide bond. For example, the carboxyl group of fatty acid 60 may react with an amino group of protein 16 to form an amide bond therewith. The methyl group of fatty acid 60 will then be electrostatically associate with a carbonyl group of protein 14 to form an organic linkage such as linkage 41 or 43. Conversely, the carboxyl group of fatty acid 60 can react with an amino group of protein 14, and its methyl group can become associated with a carbonyl group of protein 16, to form organic linkages such as linkages 42 and 44.

As seen in FIG. 2, each of linkages 41-44 has an R group (designated $R_{11}$, $R_{12}$, $R_{13}$, $R_{14}$, respectively). All of these R groups are represented generally by R in FIG. 4, and each of these R groups comprises a chain of carbon atoms from about 6 to about 48 carbon atoms long in order to provide organic linkages 41-44 with carbon chains having a total length from about 8 to about 50 carbon atoms long. Presently, the most preferred length for each of the R groups is between 12 and 18 carbon atoms long, such that each of organic linkages 41-44 is from about 14 to about 20 carbon atoms in length. Additionally, it will be appreciated that each of $R_{11}$, $R_{12}$, $R_{13}$, or $R_{14}$ may also have various carbon side chains. $R_{11}$-$R_{14}$ may be any component that may be desirable for a particular application, e.g., vitamins, enzymes, or hormones.

It is also important to note that it is not essential that each of the R groups be of the same length; indeed, it has presently been found more desirable to vary the lengths of each of these R groups so that linkages 41-44 are of differing lengths. This arrangement provides better linkage between proteins 14 and 16 in their three-dimensional configurations and further acts as a cushion between the two proteins to provide a more stable and durable structure. Finally, it will be recognized that both saturated and unsaturated fatty acids may be used to form linkages 41-44.

From the foregoing, it will be appreciated that the important chemical groups which each of fatty acids 60 need are the carboxyl and the methyl group which react to form linkages 41-44 as described herein. It will be further appreciated that alcohols such as alcohols 51-54 may be used to form linkages between alpha-lactalbumin proteins 14 and bacitracin proteins 16, in lieu of or in combination with the fatty acids discussed hereinabove. Such alcohols would form linkages in a similar fashion to linkages 31-34, discussed herein. For reasons similar to those discussed above with respect to organic linkages 31-34, the preferred length for organic linkages 41-44 is from about 14 to about 20 carbon atoms in length.

FIGS. 5 and 5A illustrate the bonding of each of the selenium ions in the compounds of the present invention to a corresponding bacitracin molecule. More particularly, FIGS. 5 and 5A provide an illustration of the bonding of a selenium ion 24 to the terminal cysteine and isoleucine amino acid residues which are found on each bacitracin molecule 16. The isoleucine residue is at the amino terminal end of bacitracin molecule 16 (at the right of FIGS. 5 and 5A) and the cysteine residue is the next amino acid residue in the bacitracin chain of amino acids (shown at the left of FIGS. 5 and 5A). Thus, FIGS. 5 and 5A represent only a small portion (the terminal two amino acids) of the long polypeptide chain which makes up each bacitracin molecule 16 illustrated in FIG. 1. (The wavy line in FIG. 5A is a representation of the continuation of the polypeptide chain).

In a typical bacitracin molecule, the sulfhydryl group of the cysteine residue and the carbonyl group of the isoleucine residue exhibit a type of tautomerism in which the hydrogen of the sulfhydryl group is transferred to the carbonyl group to form a hydroxyl group while forming a sulfide bridge between the cysteine and the isoleucine residues. In the present invention, each selenium ion is substituted for the sulfur atom which is normally associated with the sulfide bond between the adjacent isoleucine and cystine amino acid residues of each bacitracin molecule. This substitution results in a selenium bridge between the cysteine and isoleucine residues, thereby forming a molecule of seleno-bacitracin.

Referring now again to FIG. 1, zinc ions 22 may be included in multiprotein compound 10 in order to link adjacent bacitracin molecules 16 in an ionic bond. Each zinc ion 22 associates with a negatively charged carboxyl group on each of two adjacent bacitracin molecules 16 to form the zinc salt. Zinc ions 22 add desirable chemical stability to the overall structure of multiprotein compound 10. Therefore, the presence of zinc ions 22 results in a slow down of the normal degradation processes and an increase in the effective lifetime of the multiprotein compounds.

It should be noted that the exact location of each of organic linkages 18 and 20 of FIG. 1 (corresponding to organic linkages 31-34 and 41-44 of FIG. 2, respectively) is determined in large part by the reaction conditions under which multiprotein compound 10 is formed; the presently preferred reactions are explained hereinafter. By carefully controlling the reaction conditions, the actual amino acid residues which provide the sites for such linkages may be predicted with surprising accuracy.

Although the preferred procedure for preparing the compounds of the present invention may differ slightly according to the end use for which the compound is intended, the following components listed in Table I below and the methods of manufacture discussed hereinafter are given by way of general instruction to enable those of ordinary skill in the art to make multiprotein compounds which are within the scope of the present invention.

TABLE I

| Component | Weight % of Compound (preferred range) |
| --- | --- |
| beta-lactoglobulin | 40-60% |
| alpha-lactalbumin | 10-20% |
| fatty acids | 5-31% |
| zinc bacitracin | 11-25% |
| selenium (either as Se° or SeS) | 0.5-1% |
| lanolin U.S.P. (hydrous or anhydrous) | 7-20% |

As listed above, the important components of the multiprotein compounds of the present invention include beta-lactoglobulin, alpha-lactalbumin, fatty acids, zinc bacitracin, selenium (either as selenium alone or as selenium monosulfide), and lanolin U.S.P. (either hydrous or anhydrous—there is presently no known reason for preferring one over the other). Lanolin U.S.P. is an important component only in that it provides a source for the noncyclic aliphatic 51, steroid 52, and triterpenoid 53 alcohols used to form linkages 18 and for some of the fatty acids which form linkages 20. However, it should be noted that other sources for alcohols 51-53 and fatty acids 60 may be employed in lieu of lanolin U.S.P. Moreover, it should be further noted that esters of alcohols 51-53 and fatty acids 60 may be employed in lieu of or in combination with alcohols 52-53 and fatty acids 60 in making multiprotein compounds within the scope of the present invention, the ester bonds of such compounds being hydrolyzed during the manufacturing procedure to yield the alcohols and fatty acids used to form linkages 31-34 and 41-44, respectively.

Other components are often desirable in the manufacture of the compounds of the present invention, but are not critical to the function of the compounds of the present invention for their intended purpose. For example, tartaric and benzoic acid may be added to function as preservatives; these organic acids act to kill the lactobacillus bacteria which feed on the beta-lactoglobulin and the alpha-lactalbumin proteins. petrolatum U.S.P. may be added to the compounds of the present invention as an emollient or protectorate for the skin and to provide stabilization for the organic linkages 20 between proteins 14 and 16 of the present invention. ("Medium" petrolatum U.S.P. is presently preferred over "heavy" or "light" petrolatum U.S.P. since medium petrolatum U.S.P. contains a greater variety of different lengths of organic components which tends to augment the stabilization of linkages 20.) Ethanol may also be added to break the micelles in the petrolatum and lanolin (either anhydrous or hydrous), thereby reducing the temperature required for making the compounds of the present invention.

Glycerol may be added as a component in order to provide thioglycerol when it is desirable to form organic linkages between proteins 12 and 14 such as linkage 34. To generate the thioglycerol needed to form these linkages, glycerol and selenium monosulfide (instead of selenium alone) are preferably used to make the multiprotein compound 10, because the sulfur from the selenium monosulfide is released and subsequently combined with the glycerol to form thioglycerol.

One procedure for combining the above-identified components to manufacture the multiprotein compounds of the present invention is as follows: A first fraction is prepared by heating the lanolin U.S.P. to about 30°-55° C., with the presently preferred range being about 35°-40° C. If petrolatum U.S.P. is to be included, the petrolatum is mixed with the lanolin before heating to this temperature. Additionally, the optional ethanol and glycerol ingredients, if used, are added to the petrolatum-lanolin mixture, while maintaining the temperature between about 30°-55° C. (preferably at about 35°-40° C.) Although it is possible to prepare the first fraction at temperatures above about 55° C., substantial oxidation of the alcohol and fatty acid components of lanolin tends to make such elevated temperatures undesirable. Temperatures of at least about 30° C. are typically needed, however, to provide the necessary thermal energy to break up the lanolin micelles.

In a separate receptacle, a second fraction is prepared by first mixing the fatty acids together with a basic buffer solution. By this procedure, the fatty acids are converted into potassium or sodium salts in a neutralization reaction. This neutralization reaction is typically conducted at a temperature within the range of about 20°-25° C. for a period of about 2-3 hours. The buffer solution may comprise, for example, such basic constituents as sodium carbonate, sodium bicarbonate, potassium carbonate, potassium bicarbonate, or combinations thereof. Enough of a basic buffer is added to the acidic mixture to bring the pH of the mixture within the range of about 4.0-5.8, the presently preferred pH being about 5.5. Next, the optional preservative ingredients, benzoic acid and tartaric acid, are blended with the fatty acid salts and the pH is again adjusted to about 4.0-5.8 by adding more buffer. Thereafter, the components of both the first and second fractions are mixed together and allowed to react for a period of at least about 2 hours, while maintaining the pH at about 4.0-5.8 and cooling the mixture to about 20°-40° C., preferably within the range of about 25°-30° C.

Although it is possible to conduct the above procedure at pH values greater than about 5.8, the formation of organic linkages 31-34 and 41-44 decreases substantially at pH values higher than about 5.8. Also, it has been found that the final pH value for the multiprotein compound should not be lower than about 4 or higher than about 8 since multiprotein compounds having these pH values tend to cause undesirable acid-base reactions with the skin and body cells and also have shorter shelf-lives.

Moreover, it should be recognized that although the above-described procedure contains several buffer addition steps to maintain the pH within the preferred range of about 4.0–5.8 while forming the organic linkages, the procedure may be conducted using only one such buffer addition step or as many as desired in order to adjust the pH to about 4.0–5.8. It is preferable, however, to monitor and adjust the pH in several steps to ensure that the pH is indeed within the preferred range so as to ensure proper formation of the organic linkages. Finally, it is important to note that once the organic linkages are formed, the preferred range for the final pH of the multiprotein compound made is about 4.0–8.0.

While maintaining the mixture at a temperature within the range of about 20°–40° C. (preferably within the range of about 25°–30° C.), the zinc bacitracin and selenium monosulfide (or selenium alone) are introduced into the mixture and blended therewith. The resulting mixture is then cooled to room temperature, and the beta-lactoglobulin and alpha-lactalbumin are thoroughly blended into the mixture. Again, the pH should be monitored and adjusted, if necessary, with the buffer solution so as to maintain the pH at about 4.0–5.8 and enable the organic linkages to form.

In one preferred embodiment, the final pH of multiprotein compound 10 is about 5.5. By making multiprotein compound 10 with a final pH of about 5.5, the compound will be absorbed more readily by the skin which normally also has a pH of about 5.5. It will be recognized, however, that multiprotein compound 10 can be made in active form at different pH values, and that the adjustment of the pH to about 5.5 is used merely to render the compound more suitable for topical application. Moreover, a pH of about 5.5 is extremely suitable for surgical application or injection since such a pH enhances absorption of multiprotein compound 10 into the cells themselves. Cell membranes and cell nuclei generally have a pH of about 5.5, while the cytoplasm of most cells has a pH somewhere around 7.2. When multiprotein compound 10 is made with a pH of about 5.5, the natural pH differential in the cells creates an osmotic driving force which enhances absorption of the multiprotein compound by the cells.

In some instances, it may be desirable to make zinc seleno-bacitracin alone, without lactoglobulin proteins 12, lactalbumin proteins 14, and linkages 18 and 20. To make such zinc seleno-bacitracin compounds, zinc bacitracin and selenium (either in the form of selenium monosulfide or selenium alone) are mixed together in a suitable medium while preferably maintaining the pH within the range of about 4.0–5.8 (the presently preferred pH being about 5.5) at a temperature within the range of about 20°–50° C. (the presently preferred range being about 25°–30° C.). One suitable medium for making zinc seleno-bacitracin is the mixture of fractions one and two described above with respect to the manufacture of the multiprotein compound 10.

It should be recognized, however, that other mediums are also suitable for making zinc seleno-bacitracin. A suitable medium is generally any medium which is both amphocellic and hydrophilic. The amphocellic nature of the medium refers to the fact that the medium is both water and oil soluble. The primary reason that an amphocellic medium is presently preferred is that bacitracin is amphocellic; thus, an amphocellic medium is needed to effectively solvate the zinc bacitracin used to manufacture zinc seleno-bacitracin. Moreover, when selenium monosulfide (instead of selenium alone) is reacted with the zinc bacitracin to form zinc seleno-bacitracin, removal of water from the reaction medium tends to promote the reaction. Thus, a hydrophilic reaction medium is preferred when selenium monosulfide is used as the selenium reactant.

The chemical equations for reacting zinc bacitracin with selenium monosulfide (reaction A), or alternatively, with selenium alone (reaction B), are as follows:

OR

By adding glycerol to the reactants side of equation A or B, thioglycerol is also produced, together with the zinc seleno-bacitracin, since the glycerol traps the sulfide ions released from the zinc bacitracin (reactions A and B) and from the selenium monosulfide (reaction A). Generally, it is preferred to use selenium monosulfide when thioglycerol is a desired product since the use of selenium monosulfide provides twice as much available sulfur for the production of thioglycerol than where selenium alone is used.

Whenever the term "zinc seleno-bacitracin" is used herein, it will be recognized that this refers to the zinc salt of seleno-bacitracin. Also, it will be recognized that, depending upon the compound to be produced, seleno-bacitracin may be substituted for zinc seleno-bacitracin. As discussed above, the zinc functions mainly to stabilize the structure of multiprotein compound 10 and to allow the compound 10 to be subjected to higher temperatures without undergoing degradation. Accordingly, the reactions for forming seleno-bacitracin are similar to those for zinc seleno-bacitracin:

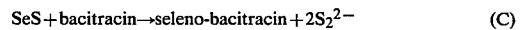 (C)

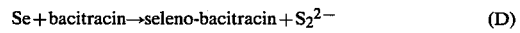 (D)

Moreover, it should be recognized that other cations may be used in lieu of zinc ions to form a salt with the bacitracin molecules and thereby provide additional stability to multiprotein compound 10. For example, any cations having a 2+ charge which are nontoxic to the body may be used, e.g., $Ca^{2+}$, $Ba^{2+}$, $Fe^{2+}$, $Mn^{2+}$, $Mg^{2+}$, etc.

The relative proportions of the components used to make the multiprotein compounds of the present invention may vary somewhat from the proportions given above, according to the intended use of the compound. Examples of compounds which are within the scope of the present invention are given hereinbelow.

EXAMPLE 1

A multiprotein compound within the scope of the present invention was made by combining the following components in the indicated amounts:

| Component | Amount (grams) |
| --- | --- |
| beta-lactoglobulin | 40 g. |
| alpha-lactalbumin | 10 g. |
| fatty acids | 14.5 g. |
| zinc bacitracin | 11.5 g. |
| selenium monosulfide | 1.0 g. |
| lanolin U.S.P. | 11.5 g. |
| tartaric acid | 1 g. |

| Component | Amount (grams) |
| --- | --- |
| benzoic acid | 2 g. |
| petrolatum U.S.P. | 6 g. |
| ethanol (70%) | 0.5 g. |
| glycerol | 2.5 g. |

These components were combined according to the following procedure: A first fraction was prepared by mixing the lanolin U.S.P., petrolatum U.S.P., ethanol, and glycerol together and the mixture was heated to and maintained at a temperature of about 40° C.

In a separate receptacle, a second fraction was prepared by first mixing the fatty acids (in the present example, 10 grams of stearic acid and 4.5 grams of oleic acid), tartaric acid, and benzoic acid together with about 2.1 grams of a buffer solution comprising 40% sodium carbonate at a temperature of about 25° C., the resulting pH of the mixture being about 5.5. This component mixture comprising the second fraction was continuously blended for a period of about 2.5 hours while maintaining the temperature at about 25° C. Thereafter, the components of the first and second fractions were mixed together and allowed to react, while the pH was maintained at about 5.5 by adding more of the buffer solution (in this example, about 0.1 grams) and the resulting mixture was allowed to cool to about 30° C.

While maintaining the mixture at 30° C., the zinc bacitracin and selenium monosulfide were introduced into the mixture and blended therewith. The resulting mixture was then cooled to room temperature, i.e. about 22° C., and the beta-lactoglobulin and alpha-lactalbumin were thoroughly blended into the mixture. The pH was again adjusted to about 5.5 by adding more of the sodium carbonate buffer solution (in this example, about 0.15 grams). This reaction mixture was allowed to react for a period of about 2.5 hours, thereby forming a multiprotein compound within the scope of the present invention.

EXAMPLE 2

A zinc seleno-bacitracin compound within the scope of the present invention was made by combining the following components in the indicated amounts:

| Component | Amount (grams) |
| --- | --- |
| zinc bacitracin | 28.85 g. |
| selenium monosulfide | 2.22 g. |
| lanolin U.S.P. | 100 g. |

These components were combined according to the following procedure: The zinc bacitracin was mixed together with the selenium monosulfide in the lanolin U.S.P. medium (lanolin provides a suitable amphocellic and hydrophilic medium for carrying out the procedure), and the mixture was heated to about 35° C. This mixture was allowed to react for a period of about 2.5 hours, thereby producing a zinc seleno-bacitracin compound within the scope of the present invention. The pH of the compound was then adjusted to about 5.5 by the addition of 2.5 grams of solid sodium bicarbonate.

EXAMPLE 3

A zinc seleno-bacitracin compound within the scope of the present invention was made by combining the following components in the indicated amounts:

| Component | Amount (grams) |
| --- | --- |
| zinc bacitracin | 28.85 g. |
| selenium | 1.57 g. |
| lanolin U.S.P. | 150 g. |
| oleic acid | 50 g. |
| ethylene glycol | 5 g. |

These components were combined according to the following procedure: The zinc seleno-bacitracin and selenium were mixed together with the lanolin and oleic acid, the lanolin and oleic acid serving as the reaction medium. The ethylene glycol was added to the mixture and the mixture was heated to about 40° C. and allowed to react for a period of about 2.5 hours, thereby producing a zinc seleno-bacitracin compound (with a pH of about 5.6) within the scope of the present invention. In this example, the ethylene glycol serves to trap the sulfur ions released from the zinc bacitracin, thereby eliminating unpleasant sulfur odors.

EXAMPLE 4

A seleno-bacitracin compound within the scope of the present invention was made by combining the following components in the indicated amounts:

| Component | Amount (grams) |
| --- | --- |
| bacitracin | 28.2 g. |
| selenium monosulfide | 2.22 g. |
| petrolatum U.S.P. | 100 g. |
| stearic acid | 15 g. |
| cholesterol | 35 g. |
| glycerol | 10 g. |

These components were combined according to the following procedure: The bacitracin and selenium monosulfide were mixed together with the petrolatum, stearic acid, and cholesterol, the petrolatum, stearic acid, and cholesterol serving as the reaction medium. The glycerol was added to the mixture and the mixture was heated to about 30° C. and allowed to react for about 2.5 hours, thereby producing a seleno-bacitracin compound (with a pH of about 5.8) within the scope of the present invention. The glycerol in the foregoing example serves merely to trap the sulfur ions released from the bacitracin and selenium monosulfide, thereby eliminating unpleasant sulfur odors.

The multiprotein compounds of the present invention have exhibited antimitotic activity in slowing down the proliferation of corneocytes without harming normal cells. The active ingredient of multiprotein 10 in treating psoriasis is believed to be the zinc seleno-bacitracin. In particular, the zinc seleno-bacitracin molecules to act to deliver selenium ions to the deoxyribonucleic acid of the corneocytes so as to prohibit mitosis.

During the early stages of mitosis, it is believed that negative charges on each of the deoxyribonucleic acid strands cause the deoxyribonucleic acid to begin to unwind, thus beginning replication. By delivering a selenium ion (having a +2 charge) to the deoxyribonucleic acid, the selenium ion becomes incorporated into one of the deoxyribonucleic acid strands, thereby imparting a net positive charge to that strand and causing the two strands to be attracted together, instead of being repelled as is needed for the unwinding action of replication. In this manner, the selenium ion can prohibit the replication of the deoxyribonucleic acid, and thus the replication of the corneocytes. As will be discussed hereinafter, this action of the selenium ions does not affect the normal growth of normal cells.

The bacitracin molecule 16 provides a chemical transport structure for each selenium ion 24; each bacitracin molecule delivers the selenium ion to the deoxyribonucleic acid of a corneocyte. The alpha-lactalbumin protein 14 and beta-lactoglobulin protein 12 with their accompanying linkages 20 and 18, provide a chemical support structure for the zinc seleno-bacitracin.

Moreover, the alpha-lactalbumin protein 14 provides a means for effectuating entry of multiprotein compound 10 into the corneocytes. This is made possible by the hydrolyzing properties of alpha-lactalbumin protein 14. Alpha-lactalbumin protein 14 acts to hydrolyze the beta-1→4 linkages between N-acetylmuramic acid and 2-acetylamino-2-deoxy-D-glucose in mucopolysaccharides and mucopeptides and to break the bonds in teichoic acid. These constituents are all important components in the structure of the cell wall, and upon hydrolyzation thereof, allow entry of the multiprotein compound into the cell.

After hydrolyzing the cell wall structure to allow entry of the multiprotein compound into the cell, the hydrolysis performed by the alpha-lactalbumin protein 14 is reversed to restore the cell wall. The reverse hydrolysis or restoration of the cell wall is accomplished by the bacitracin portion of the zinc seleno-bacitracin. Bacitracin has the capacity to absorb a significant amount of water and thus acts to absorb the water molecules which were added to the cell wall during hydrolysis, thereby reversing the hydrolysis and restoring the cell wall to its original stature. Thus, the multiprotein compound of the present invention provides means for entering the cell without harming the cellular structure.

The beta-lactoglobulin protein 12 of the multiprotein compound adds stability to the overall structure of the compound. More importantly, in combination with organic linkages 18, beta-lactoglobulin protein 12 acts to increase the hydrolyzing activity of alpha-lactalbumin protein 14 by slowing down the rotational movement about the carbon-to-carbon bonds of the polypeptide chain of alpha-lactalbumin protein 14 by a factor of at least 100. Thus, beta-lactoglobulin protein 12 and linkages 18 serve to enhance the capacity of alpha-lactalbumin protein 14 to hydrolyze the cell wall and facilitate entry of multiprotein compound 10 into the cell.

Once inside the cell, it is believed that cellular enzymes act to hydrolyze the bonds between linkages 18 and beta-lactoglobulin protein 12 so as to detach beta-lactoglobulin protein 12 from the remainder of the structure of multiprotein compound 10. Beta-lactoglobulin proteins 12 are subsequently attacked by cellular proteinases which degrade these proteins 12 into amino acids which can be used by the body. Further, the positively charged selenium ion and the positively charged methyl groups on the free ends of linkages 18 (once detached from beta-lactoglobulin protein 12) can be attracted to the negatively charged deoxyribonucleic acid in the nucleus of the cell, thereby providing the necessary driving force for delivering the selenium ion to the deoxyribonucleic acid.

Upon arrival of the deoxyribonucleic acid, the remaining portion of multiprotein compound 10 releases the selenium ion which combines with the deoxyribonucleic acid to stop replication thereof. The remaining portion of multiprotein compound 10 is then attacked by proteinases and other enzymes found in the cell to yield amino acids (originating from proteins 14 and 16), fatty acids (originating from linkages 20), and a variety of alcohols (originating from linkages 18) which may subsequently be used by the body. Thus, the multiprotein compound of the present invention is broken down like any other protein to be used as food and to provide amino acids for the manufacture of other proteins needed by the body.

Importantly, since the multiprotein compound enters normal cells as well as corneocytes, it should be noted that the multiprotein compound does not act to destroy any cells, whether corneocytes or normal cells, but rather acts to prohibit proliferation and growth of the corneocytes alone. This is believed to be due to the fact that the selenium ions 24 delivered by the multiprotein compound only act momentarily to prohibit replication of the deoxyribonucleic acid, thereby giving the corneocytes enough time to repair and rehabilitate themselves into normal cells.

The abnormal or rapid proliferation of corneocytes which causes psoriasis results in corneocytes which are often deficient. Deficient corneocytes generally have the capacity to be repaired or rehabilitated, but usually cannot repair themselves without some assistance. Since, as will be discussed in greater detail hereinafter with regard to scar tissue and wound healing, the multiprotein compounds of the present invention provide most, if not all, of the raw materials necessary to help the deficient corneocytes repair themselves, multiprotein compound 10 actually promotes the repair of the deficient corneocytes into "normal" cells. Thus, the multiprotein compounds give the deficient corneocytes time to repair themselves before further replication of these cells can occur and further act to actually promote such repair, while leaving the normal cells unharmed.

The following components listed in Table II below and examples discussed hereinafter are given by way of general instruction to enable those of ordinary skill in the art to make other multiprotein compounds within the scope of the present invention.

TABLE II

| Component | Weight % of Compound (preferred range) |
|---|---|
| beta-lactoglobulin | 40–60% |
| alpha-lactalbumin | 10–20% |
| fatty acids | 5–20% |
| zinc bacitracin | 15–24% |
| selenium (either as Se° or SeS) | 0.7–1.0% |
| glycerol | 1–5% |
| tartaric acid | 1–3% |
| lanolin U.S.P. | 7–15% |

The components listed above are combined in the same manner as outlined in Example I, with the exception that certain of the components of Example I are omitted. It should be noted that although preferred ranges are given for glycerol and tartaric acid, these components are purely optional when making a multiprotein compound within the scope of the present invention.

EXAMPLE 5

A multiprotein compound within the scope of the present invention was made according to the procedure of Example 1, except that the components were combined in the following amounts:

| Component | Amount (grams) |
| --- | --- |
| beta-lactoglobulin | 48 g. |
| alpha-lactalbumin | 12 g. |
| fatty acids | 6 g. |
| zinc bacitracin | 24 g. |
| selenium monosulfide | 1.4 g. |
| glycerol | 1 g. |
| tartaric acid | 1 g. |
| lanolin U.S.P. (anhydrous) | 7 g. |

In this example, the fatty acids used were oleic acid (5 grams) and palmitic acid (1 gram).

EXAMPLE 6

Another multiprotein compound within the scope of the present invention was made according to the procedure of Example 5, except that 0.5 grams of ethanol were added to the lanolin. The addition of ethanol aids in breaking up the lanolin micelles.

2. Methods of Treatment

A. Psoriasis

The action of the multiprotein compounds of the present invention in the treatment of psoriasis is believed to be as follows. It is believed that multiprotein compound 10 acts to prohibit replication of the deoxyribonucleic acid in the corneocytes (white skin cells), thereby slowing down proliferation of the corneocytes while leaving normal cells unharmed. Multiprotein compound 10 accomplishes this by providing a mechanism for transporting selenium ions to the deoxyribonucleic acid in the corneocytes so as to prevent unwinding and thus replication of the deoxyribonucleic acid.

The following components listed in Table III below and example discussed hereinafter are given by way of general instruction to enable those of ordinary skill in the art to make multiprotein compounds within the scope of the present invention which may be used in the treatment of psoriasis.

TABLE III

| Component | Weight % of Compound (preferred range) |
| --- | --- |
| beta-lactoglobulin | 40–60% |
| alpha-lactalbumin | 10–20% |
| fatty acids | 5–20% |
| zinc bacitracin | 12–20% |
| selenium (either as Se° or SeS) | 0.5–0.7% |
| lanolin U.S.P. | 7–20% |
| petrolatum U.S.P. | 0–5% |
| glycerol | 0–4% |
| tartaric acid | 1–3% |
| benzoic acid | 1–5% |
| ethanol | 0.5–1% |

The components listed above are combined in the same manner as outlined in Example 1. It should be noted that although preferred ranges are given for petrolatum, glycerol, tartaric acid, benzoic acid, and ethanol, these components are purely optional when making a multiprotein compound within the scope of the present invention for the treatment of psoriasis.

EXAMPLE 7

A multiprotein compound within the scope of the present invention which has been used in the treatment of psoriasis was made according to the procedure of Example 1, except that the components were combined in the following amounts:

| Component | Amount (grams) |
| --- | --- |
| beta-lactoglobulin | 48 g. |
| alpha-lactalbumin | 12 g. |
| fatty acids | 7 g. |
| zinc bacitracin | 19.3 g. |
| selenium monosulfide | 0.8 g. |
| lanolin U.S.P. (hydrous) | 7 g. |
| petrolatum U.S.P. | 2.5 g. |
| glycerol | 1 g. |
| tartaric acid | 1 g. |
| benzoic acid | 1.5 g. |
| ethanol | 0.5 g. |

In this example, the fatty acids used were stearic acid (5 grams) and oleic acid (2 grams). This multiprotein compound has been used for the treatment of psoriasis. The daily dosage for such applications ranges from about 0.001–0.2 g/cm$^2$ of skin treated. A typical treatment using this multiprotein compound would include two daily topical applications of 0.04–0.1 grams of the compound per square centimeter of skin treated.

Although animal studies are continuing, at least a dozen psoriasis patients have received treatment using the compound of Example 7. Marked improvements in the conditions of these patients were noted within three weeks of treatment.

B. Arthritis

When used in the treatment of arthritis, the active ingredient of the multiprotein compounds of the present invention is believed to be the alpha-lactalbumin protein 14. Alpha-lactalbumin protein 14 acts to break up polymerized collagen which is the major cause of arthritis. Alpha-lactalbumin protein portion 14 of multiprotein compound 10 accomplishes this by hydrolyzing the glucosyl linkages in the polymerized collagen, and also acts to prohibit further polymerization of the collagen.

The beta-lactoglobulin protein 12, and further the bacitracin proteins 16, act primarily to stabilize the overall structure of multiprotein compound 10 and increase the hydrolyzing activity of alpha-lactalbumin protein 14 when used in the arthritis treatment of the present invention. Under normal conditions, it has been found that alpha-lactalbumin by itself will only hydrolyze about 3% of polymerized collagen, the hydrolyzing activity of alpha-lactalbumin alone being relatively limited. However, when alpha-lactalbumin is linked to beta-lactoglobulin by a plurality of organic linkages within the scope of the present invention, a much higher percentage of hydrolysis, if not nearly complete hydrolysis, of the polymerized collagen is achieved.

The following components listed in Table IV below and examples discussed hereinafter are given by way of general instruction to enable those of ordinary skill in the art to make multiprotein compounds within the scope of the present invention which may be used in the treatment of arthritis.

TABLE IV

| Component | Weight % of Compound (preferred range) |
| --- | --- |
| beta-lactoglobulin | 40–60% |

TABLE IV-continued

| Component | Weight % of Compound (preferred range) |
| --- | --- |
| alpha-lactalbumin | 10-20% |
| fatty acids | 5-31% |
| zinc bacitracin | 12-24% |
| selenium (either as Se° or SeS) | 0.5-1.0% |
| lanolin U.S.P. | 7-20% |
| glycerol | 1-5% |
| tartaric acid | 0-3% |
| benzoic acid | 1-5% |
| ethanol | 0.5-1.5% |

The components listed above are combined in the same manner as outlined in Example 1, with the exception that certain of the components of Example 1 are omitted. It should be noted that although preferred ranges are given for zinc bacitracin, selenium, glycerol, tartaric acid, benzoic acid, and ethanol, these components are purely optional when making a multiprotein compound within the scope of the present invention for the treatment of arthritis.

EXAMPLE 8

A multiprotein compound within the scope of the present invention which has been used in the treatment of arthritis was made according to the procedure of Example 1, except that the components were combined in the following amounts:

| Component | Amount (grams) |
| --- | --- |
| beta-lactoglobulin | 53.5 g. |
| alpha-lactalbumin | 13.5 g. |
| fatty acids | 10 g. |
| zinc bacitracin | 11 g. |
| selenium monosulfide | 1.4 g. |
| lanolin U.S.P. (anhydrous) | 7 g. |
| glycerol | 1 g. |
| tartaric acid | 1 g. |
| benzoic acid | 2 g. |
| ethanol | 0.5 g. |

In this example, the fatty acids used were stearic acid (8 grams) and oleic acid (2 grams). It should be noted that the addition of petrolatum U.S.P. is not generally desirable when preparing multiprotein compounds for the treatment of arthritis. This is because substantial quantities of petrolatum tend to decrease the hydrolyzing activity of alpha-lactalbumin and such hydrolyzing activity is a key factor in the treatment of arthritis.

It should also be recognized that the zinc seleno-bacitracin portion of multiprotein compound 10 is optional when using the multiprotein compound for the treatment of arthritis. The bacitracin proteins 16 and linkages 20 do act to further enhance the hydrolyzing properties of alpha-lactalbumin proteins 14, but the multiprotein compound has been found to be effective in treating arthritis without the bacitracin proteins 16, organic linkages 20, and selenium ions 24. (The selenium ions 24 do not act to increase hydrolyzing activity, but may be desirable for other reasons, e.g., some of the selenium ions may be converted into trimethyl selenonium which is beneficial to the body.)

EXAMPLE 9

A multiprotein compound within the scope of the present invention useful in the treatment of arthritis was made by combining the following components in the following amounts:

| Components | Amount (grams) |
| --- | --- |
| beta-lactoglobulin | 60 g. |
| alpha-lactalbumin | 16.5 g. |
| fatty acids | 8.5 g. |
| lanolin U.S.P. | 8.5 g. |
| tartaric acid | 1.0 g. |
| ethanol (95%) | 0.5 g. |
| safflower oil | 5.0 g. |

In this example, the fatty acids used were stearic acid (3.5 grams), arachidonic acid (1 gram), and linoleic acid (4 grams). These components were combined according to the following procedure: A first fraction was prepared by mixing the lanolin U.S.P., safflower oil, and ethanol together, and the mixture was heated to and maintained within a temperature range of about 35°-40° C.

In a separate receptacle, a second fraction was prepared by mixing the fatty acids and tartaric acid together with about 1.6 grams of solid potassium carbonate buffer at a temperature of about 23° C., the resulting pH of the mixture being about 5.5. This component mixture comprising the second fraction was continuously blended for a period of about 2.5 hours while maintaining the temperature at about 23° C. Thereafter, the components of the first and second fractions were mixed together and allowed to react, while the pH was maintained at about 5.5 by adding about 0.2 grams of a solid sodium carbonate buffer and the resulting mixture was allowed to cool to about 23° C.

In another receptacle, a third fraction was prepared by mixing the beta-lactoglobulin and alpha-lactalbumin together at a temperature of about 23° C. The third fraction was then added to the already combined first and second fractions and blended thoroughly. The pH was again adjusted by adding 0.1 grams of solid potassium carbonate buffer. This mixture was allowed to react for a period of about 2.5 hours, thereby producing a multiprotein compound within the scope of the present invention which is useful in the treatment of arthritis.

Although application by injection is also possible, the multiprotein compound 10 is generally applied topically when used to treat arthritis. When applied topically, multiprotein compound 10 penetrates the skin and reaches the arthritic joint within about ten (10) to about fifteen (15) minutes. Thus, although injection of the multiprotein compound 10 directly into the joints is equally effective, topical application is often preferred because of the relative convenience of application. Topical applications should provide a daily dosage of about 0.001–0.2 grams per square centimeter (g/cm$^2$) of skin. A presently preferred method for applying the multiprotein compound 10 to arthritis comprises applying 0.04–0.1 g/cm$^2$ of the compound to the skin twice daily. Such treatment should continue on a daily basis until the arthritic pain disappears and freedom of movement is restored.

While additional studies are in progress, at least two individuals have been treated for arthritis using the compound of Example 8. Both of these individuals had severe diagnosed cases of arthritis, the symptoms of which cleared up after regular treatment over a period of about three weeks with this multiprotein compound.

C. Erythropietic Protoporphyria

The multiprotein compounds of the present invention have been found to be effective in treating the symptoms of erythropoietic protoporphyria. As porphyrin IX accumulates in the cells (as is characteristic of erythropoietic protoporphyria), the porphyrin IX reacts with the cell walls, causing a swelling and splitting of the skin. The multiprotein compounds of the present invention act to alleviate such swelling and splitting. Although the exact mechanism for this action is not completely understood, it is believed that in the treatment of erythropoietic protoporphyria, the active ingredients of the multiprotein compounds are beta-lactoglobulin protein 12 and linkages 18 attached thereto. As the multiprotein compound enters the cell, the presence of porphyrin IX is believed to cause the bonds between linkages 18 and alpha-lactalbumin 14 to break, thereby releasing beta-lactoglobulin protein 12 with linkages 18 attached thereto. The free hydroxyl groups at the unattached ends of linkages 18 then react with the carboxyl groups of porphyrin IX to form ester-type bonds therewith. Thus attached, beta-lactoglobulin protein 12 places stress on the prophyrin IX (applying a type of "pulling" action) thereby inhibiting prophyrin IX from accumulating so many water molecules. This, in turn, reduces the swelling, and gives the cell more time to degrade the prophyrin IX. Whatever the mechanism of multiprotein compound 10 in treating the symptoms of erythropoietic protoporphyria, it is clear that multiprotein compound 12 acts to alleviate the symptoms of swelling and splitting of the skin caused by the accumulation of porphyrin IX.

As mentioned hereinabove, beta-lactoglobulin protein 12 and attached linkages 18 are believed to be the active ingredients of multiprotein compound 10 when used in a treatment for erythropoietic protoporphyria. In such a treatment, alpha-lactalbumin protein 14 serves to effectuate entry of multiprotein compound 10 into the cells, much in the same manner as with the other treatments. The bacitracin proteins 16 act to stabilize the multiprotein compound structure 10 and to increase the hydrolyzing activity of alpha-lactalbumin protein 14.

The following components listed in Table V below and examples discussed hereinafter are given by way of general instruction to enable those of ordinary skill in the art to make multiprotein compounds within the scope of the present invention which may be used in the treatment of erythropoietic protoporphyria.

TABLE V

| Component | Weight % of Compound (preferred range) |
| --- | --- |
| beta-lactoglobulin | 40-60% |
| alpha-lactalbumin | 10-20% |
| fatty acids | 15-31% |
| zinc bacitracin | 12-20% |
| selenium (either as Se° or SeS) | 0.5-0.7% |
| lanolin U.S.P. | 7-20% |
| petrolatum U.S.P. | 1-10% |
| glycerol | 0-5% |
| tartaric acid | 0-3% |
| benzoic acid | 0-2% |
| ethanol | 0.5-1.5% |

The components listed above are combined in the same manner as outlined in Example 1. It should be noted that although preferred ranges are given for alpha-lactalbumin, zinc bacitracin, selenium, petrolatum, glycerol, tartaric acid, benzoic acid, and ethanol, these components are purely optional when making a multiprotein compound within the scope of the present invention for the treatment of erythropoietic protoporphyria. It should be further noted that the fatty acids and lanolin can be used either in combination or alone to make multiprotein compounds within the scope of the present invention for the treatment of erythropoietic protoporphyria. Thus, where fatty acids are used alone, lanolin becomes an "optional" component, and conversely, where lanolin is used alone, the fatty acids become an "optional" component.

EXAMPLE 10

A multiprotein compound within the scope of the present invention which has been used in the treatment of erythropoietic protoporphyria was made according to the procedure of Example 1, except that the components were combined in the following amounts:

| Compound | Amount (grams) |
| --- | --- |
| beta-lactoglobulin | 53.5 g. |
| alpha-lactalbumin | 13.5 g. |
| fatty acid | 8 g. |
| zinc bacitracin | 11.5 g. |
| selenium monosulfide | 0.7 g. |
| lanolin U.S.P. (anhydrous) | 7 g. |
| petrolatum U.S.P. | 3 g. |
| glycerol | 1 g. |
| tartaric acid | 1 g. |
| benzoic acid | 1 g. |
| ethanol | 0.5 g. |

In this example, the fatty acid used was stearic acid (8 grams).

EXAMPLE 11

Another compound within the scope of the present invention useful in the treatment of erythropoietic protoporphyria was made by combining the following components in the indicated amounts:

| Compound | Amount (grams) |
| --- | --- |
| beta-lactoglobulin | 57 g. |
| lanolin U.S.P. | 7 g. |
| linoleic acid | 26 g. |
| glycerol | 10 g. |

These components were combined according to the following procedure: a first fraction was prepared by mixing the lanolin with the glycerol and by heating the mixture to about 40° C. In a separate receptacle, a second fraction was prepared by mixing the linoleic acid with about 1.7 grams of a 30% sodium carbonate buffer solution, thereby bringing the pH to about 5.5. The second fraction was allowed to react for about 2.5 hours at a temperature of about 24° C. while mixing thoroughly.

The components of fractions one and two were then combined and the pH was adjusted to about 5.5 by adding an additional 0.3 grams of the buffer solution. The resulting mixture was allowed to cool to about 25° C. and the beta-lactoglobulin was added to the mixture. The pH of the mixture was again adjusted to about 5.5 by adding an additional 0.1 grams of the buffer solution. This mixture was allowed to react for a period of about 2.5 hours, thereby producing a compound within the scope of the present invention suitable for the treatment of erythropoietic protoporphyria.

In treating erythropoietic protoporphyria, a compound such as that in Example 10 or 11 is generally applied topically in daily dosages of about 0.001–0.2 g/cm² of skin treated. The presently preferred daily dosage is about 0.08–0.2 g/cm² of skin treated.

One individual has been treated for erythropoietic protoporphyria with the preferred compound of Example 10. This individual had been previously treated unsuccessfully with X-rays and cortisone treatments. After receiving the erythropoietic protoporphyria treatment of the present invention for two days, the individual showed substantial symptom relief. In particular, the swollen and split hands of the individual were healed. Significantly, the disease has not recurred since the termination of treatments.

D. Scar Tissue and Wounds

It is believed that most, if not all, of the components of the multiprotein compounds of the present invention act as active ingredients in treating scar tissue and in promoting wound healing. Basically, the process of tissue regeneration requires the presence of phospholipids, sterols, and proteins. The basic building blocks of each of these components are present in the structure of the multiprotein compounds of the present invention.

For example, proteins 12, 14, and 16 are degraded by the body into amino acids which can subsequently be used to manufacture the necessary proteins for tissue regeneration. Upon degradation of the multiprotein compounds, linkages 32 are converted into steroid alcohols which are the basic building blocks for the sterols needed for tissue regeneration. Finally, upon degradation of multiprotein compounds, organic linkages 41–44 are converted into fatty acids which are the basic building blocks of the phospholipids needed for tissue regeneration.

Thus, it will be appreciated that the multiprotein compounds of the present invention supplies most, if not all, of the raw materials necessary to promote wound healing and tissue regeneration. Moreover, the bacitracin proteins 16 of the multiprotein compounds provide anti-bacterial activity necessary in wound healing and tissue regeneration.

Finally, it is believed that multiprotein compound 10 acts to promote the actual tissue regeneration mechanisms of the body. Although the precise mechanism of tissue regeneration is not completely understood, it is believed that upon introduction of the multiprotein compounds into the body, the body utilizes enzymes to break up the compounds; these enzymes are the same enzymes involved in tissue regeneration mechanisms. Thus, it is postulated that the very introduction of the multiprotein compounds into the body attracts the necessary enzymes present in the body which are responsible for tissue regeneration.

These three characteristics of multiprotein compound 10, i.e., (1) providing anti-bacterial activity, (2) providing a source of most, if not all, of the components needed for tissue regeneration, and (3) providing a means for actually promoting the tissue regeneration mechanisms of the body, combine to make the application of the multiprotein compounds an effective treatment for scar tissue and for promoting wound healing and tissue regeneration.

The following components listed in Table VI below and example discussed hereinafter are given by way of general instruction to enable those of ordinary skill in the art to make multiprotein compounds within the scope of the present invention which may be used in the treatment of scar tissue and wounds.

TABLE VI

| Component | Weight % of Compound (preferred range) |
| --- | --- |
| acetylglucosamine | 2–4% |
| beta-lactoglobulin | 50–60% |
| alpha-lactalbumin | 10–20% |
| lanolin U.S.P. | 7–15% |
| zinc bacitracin | 12–20% |
| selenium (either as Se° or SeS) | 0.5–0.7% |
| petrolatum U.S.P. | 5–10% |
| fatty acids, cysteine, & alanine | 15–31% |
| glycerol | 1–10% |
| ethanol | 0.5–1.5% |

The components listed above are combined in the same manner as outlined in Example 1, with the exception that certain of the components of Example 1 are omitted. It should be noted that although preferred ranges are given for acetylglucosamine, selenium, petrolatum U.S.P., glycerol, ethanol, cysteine, and alanine, these components are purely optional when making a multiprotein compound within the scope of the present invention for the treatment of scar tissue and wounds.

The acetylglucosamine, cysteine, and alanine are mixed with the fatty acids of the second fraction in the procedure of Example 1. Moreover, sialic acid or neuraminic acid may be substituted for acetylglucosamine.

EXAMPLE 12

A multiprotein compound within the scope of the present invention useful for the treatment of scar tissue and for promoting wound healing has been made by combining the following components in the indicated amounts:

| Component | Amount (grams) |
| --- | --- |
| acetylglucosamine | 4 g. |
| beta-lactoglobulin | 44 g. |
| alpha-lactalbumin | 11 g. |
| lanolin U.S.P. (anhydrous) | 8 g. |
| zinc bacitracin | 14.4 g. |
| selenium monosulfide | 0.7 g. |
| petrolatum U.S.P. | 5 g. |
| fatty acids | 6.5 g. |
| cysteine | 3 g. |
| alanine | 2.0 g. |
| glycerol | 1 g. |
| ethanol | 0.5 g. |

In this example, the fatty acids used were oleic acid (2 grams), elaidic acid (1 gram), palmitic acid (1.5 grams), and stearic acid (2.0 grams). From the foregoing, it will be recognized that a few additional components are included in this example of a multiprotein compound for treating scar tissue and for promoting wound healing. It should be noted that benzoic and tartaric acid preservatives may also be used in conjunction with the foregoing components. Moreover, since a common source for the beta-lactoglobulin and alpha-lactalbumin is hydrolyzed milk protein, it may also be desirable to include other components of the hydrolyzed milk protein which have been found to have a beneficial effect towards wound healing, e.g., acetylneuraminic acid, orthosialic acid, parasialic acid, glycolneuraminic acid, glycolsialic acid, and acetylsialic acid.

The foregoing components were combined as follows: A first fraction was prepared by mixing the petrolatum U.S.P. with the lanolin U.S.P., and the mixture was heated to about 35° C. Next, the ethanol was blended into the mixture while maintaining the temperature at about 35° C. A second fraction was prepared by mixing the fatty acids, cysteine, alanine, and acetylglucosamine (the tartaric acid and benzoic acid preservatives would be added here if desired) together in a separate receptacle at a temperature of about 22° C. A buffer solution of 25% potassium bicarbonate was added to the second fraction to adjust the pH to about 5.5. The second fraction was continually mixed for about 2.5 hours until fully reacted and well blended. The second and first fractions were then mixed together and cooled to about 30° C. and the pH was again adjusted to about 5.5 by adding an additional 0.3 grams of the potassium bicarbonate buffer solution. Finally, the zinc bacitracin and selenium monosulfide were blended into the mixture and the mixture was slowly cooled to about 22° C. At this temperature, the beta-lactoglobulin and alpha-lactalbumin were blended into the mixture. Subsequently, the pH was again adjusted by adding 0.1 grams of the potassium bicarbonate buffer solution to maintain the pH at about 5.5.

Multiprotein compound 10 is generally applied topically when used to treat scar tissue and to promote wound healing. The daily dosage of such applications should be within the range of about 0.001–0.2 grams per square centimeter ($g/cm^2$). The presently preferred daily dosage is about 0.08–0.2 $g/cm^2$, being administered in two daily applications of 0.04–0.1 $g/cm^2$ each.

While additional studies are continuing, the only experimental results available for the application of the multiprotein compound of the present invention for treating scar tissue and for promoting wound healing are those results reported above with regard to psoriasis. Since skin afflicted with psoriasis is generally characterized by what may be termed as "wounds," the experimental results obtained in the psoriasis treatments are also applicable to wound healing.

3. Additional Examples of Compounds of the Present Invention

Numerous other multiprotein compounds within the scope of the present invention have been made. Two hundred forty-eight of these examples are reported in tabular form in Table VII below as Examples 13–260. In each of these examples, the amount of the components used is reported in Table VII.

It is important to note that, in actuality, each of Examples 13–260 reported in Table VII represents four separate compounds made; each example of Table VII has been carried out using bacitracin, zinc bacitracin, calcium bacitracin, and magnesium bacitracin (these bacitracin components being referred to generically as "bacitracin" in Table VII).

The multiprotein compounds reported in Table VII were made according to the procedure of Example 1, with the exception that when alcohols and oils were added, they were added to the lanolin of the first fraction in the procedure of Example 1. (The oils employed are esters which provide alcohols and/or fatty acids upon hydrolysis.) The fatty acids, of course, were added to the second fraction of the procedure of Example 1. It should be noted that in the examples where selenium is employed, the selenium was introduced as selenium monosulfide, except for Examples 36–38, 60, 82, and 176 wherein selenium alone was used. However, for each of the examples of Table VII where selenium sulfide was used, the gram quantities listed for "selenium" represent the gram weight of the selenium only, not the actual weight of selenium sulfide which was added. To convert these figures to gram weights of selenium sulfide, well-known conversion factors could be employed.

In order to better understood where each component was added in the procedure of Example 1, the following categories are given as an aid in determining which of the components listed in Table VII are categorized as alcohols, oils, and fatty acids.

Alcohols: adenosine; B-caroten-3-ol; choline; colchiceine; cortisone; decyl-B-caroten-3-ol; pentyl-B-caroten-3-ol; picrotoxinin; sitosterol; stigmasterol; tocopherol.

Oils: coconut oil; corn oil; cottonseed oil; mineral oil; olive oil; palm oil; peanut oil; rice oil; safflower oil; sesame oil; soybean oil; sunflower oil; vegetable oil; wheatgerm oil.

Fatty Acids: acetylgluconic acid; acetylglucosamine; amino acids; aminobenzoic acid; aminolevulinic acid; arachidic acid; arachidonic acid; ascorbic acid; 1,3 dihydroxybenzoic acid; 2,5 dihydroxybenzoic acid; dodecanoic acid; citric acid; eicosanoic acid; eicosatrienoic acid; elaidic acid; folic acid; gluconic acid; linoleic acid; linolenic acid; meso-tartaric acid; myristic acid; nicotinic acid; oleic acid; palmitic acid; stearic acid; succinic acid; sulfamic acid; sulfanilic acid; thiophene-3-carboxylic acid; triacontanoic acid; undecanoic acid.

According to the procedure of Example 1, the alcohols and oils were added to the first fraction, and the fatty acids were added to the second fraction of that example.

TABLE VII

| COMPONENTS (GRAMS) | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|
| Lactoglobulin | 50 | 52 | 45 | 40 | 40 | 60 | 40 | 42 | 43 | 55 | 47 | 43.5 | 46 | 41 | 41.5 | 44 | 59 |
| Lactalbumin | 15 | 17 | 14 | 10 | 10 | | 15 | 10 | 13 | | 13 | 15 | 14.5 | 11 | 1.5 | 20 | |
| Bacitracin | | | 11.5 | 11.5 | 11.5 | | 24 | 19 | 12.3 | | 22 | 11.5 | 15.4 | 13 | 12.5 | | |
| Selenium | | | .5 | .5 | .5 | | 1 | 1 | .7 | | 1 | .5 | .6 | .5 | .5 | | |
| Petrolatum U.S.P. | | | 5 | | 3 | | | 4 | 3.3 | 7 | | 3.5 | | 2 | 5 | | |
| Ethanol | .5 | | | | | 1 | | .6 | .7 | .8 | | | | .9 | | | 1 |
| Lanolin U.S.P. | 12 | 15 | 18 | 14 | 7 | 20 | 7 | 12 | 10 | 20 | 8 | 13 | 12.5 | 20 | 7 | 7.5 | 18 |
| Gylcerol | 5 | 4 | | 3 | 2 | | 5 | 6 | 2.2 | | 1 | 3.5 | .5 | .6 | | | |
| Benzoic Acid | 4 | 4 | | 1 | | | | | .3 | | | | | 1 | | | |
| Tartaric Acid | 2 | 2 | | 1 | | | | | .5 | | | | | | | | |
| Citric Acid | 1.5 | | | | | | | | | | | | | | | | |
| Ascorbic Acid | 2 | | | | | | | | | | | | | | | | |
| Folic Acid | | | | 2 | 1 | | | | 1.5 | | .5 | | | | | | |
| Choline | | | | 1 | 1 | | | | .5 | | | | | | | | |
| Acetylgluconic Acid | | | 3 | 3 | | | | | | | | | | | | | |
| Picrotoxinin | | | | | | | | | 1 | | | | | | | | |
| Gluconic Acid | | | | | | | | | | | | | | | | | |
| Aminoleuulinic Acid | 1 | | | 1 | | | | | .5 | | | | | | | | |
| Succinic Acid | | | | | | | | | .2 | | | | | | | | |
| Tryptophan | | | | 1 | | | | | | | .3 | | | | | | |
| Nicotinic Acid | | | | | | | | | 1 | | .5 | | | | | | |
| Sulfanilic Acid | | | | | | | | | | | | | | | | | |
| Sulfamic Acid | | | | | | | | | .5 | | | | | | | | |
| Cortisone | 1 | | | 1 | | 2 | | | | | .2 | | | | | | 1 |
| Colchiceine | | 1 | | 1 | | | | | .5 | | .5 | | | | | | |
| Aminobenzoic Acid | | | | 1 | | | | | | | | | | | | | |
| Sitosterol | | | | | | | | | | | .5 | 1 | | | | | |
| Stigmasterol | | | | | | | 4 | | | | | | | | 3.4 | .1 | |
| Oleic Acid | | 1 | | | 2 | | | .4 | | | | .5 | | | | | |
| Stearic Acid | | 2 | 2 | | | 5 | | | | | | | | | | | |
| Arachidic Acid | | 1 | | 1 | | | 2 | | | .2 | | | | | | | |
| Arachidonic Acid | | | | | 1 | | | | | | | | | | | | |
| Elaidic Acid | | | | | 1 | 10 | 2 | 5 | | | | 8 | | 5 | | 10 | 21 |
| Linoleic Acid | | | | 1 | 2 | | | | .3 | | .5 | | | 1 | | 5 | |
| Linolenic Acid | | | 3.5 | 5 | 14 | 2 | | | 7 | 7 | 5 | | 1.5 | 4 | 23 | 5 | |
| Coconut Oil | 6 | 1 | | | | | | | | | | | | | | 5 | |

| COMPONENTS (GRAMS) | 30 | 31 | 32 | 33 | 34 | 35 | 36 | 37 | 38 | 39 | 40 | 41 | 42 | 43 | 44 | 45 | 46 | 47 | 48 | 49 | 50 | 51 |
|---|---|---|---|---|---|---|---|---|---|---|---|---|---|---|---|---|---|---|---|---|---|---|
| Lactoglobulin | 44 | 47 | 53 | 51 | 56 | 60 | 42 | 45 | 47.5 | 40 | 41 | 42 | 43 | 44 | 45 | 60 | 58 | 58.5 | 50.5 | 57.5 | 56 | 54 |
| Lactalbumin | 20 | 15 | | | | | 13 | 13 | 14 | 10 | 12 | 13 | 12 | 11 | 15 | | | | | | | |
| Bacitracin | | | | | | | 12 | 13 | 11.5 | 24 | 22 | 23 | 20 | 21 | 19.3 | | | | | | | |
| Selenium | | | | | | | | | .5 | 1 | 1 | 1 | 1 | 1 | .7 | | | | | | | |
| Petrolatum U.S.P. | .3 | | 10 | | .4 | .3 | .5 | 3.5 | .5 | 1 | 2 | 4 | 3.5 | 5 | 6 | 2.5 | 2 | 1 | 3 | 4 | | .5 |
| Ethanol | 7.2 | 7 | | .5 | 7.3 | 8 | 4 | | 2 | 2 | | | 1 | 1.5 | 1 | | | | | | | 9.5 |
| Lanolin U.S.P. | 4.5 | 4 | | 11 | | | .8 | 1.5 | 13.5 | .5 | 10 | 7.1 | 7.5 | 7.2 | 8 | 13.2 | 8 | 9 | 8.5 | 11 | 1.5 | |
| Glycerol | | | | | | | 7.3 | 1 | 2 | 8.2 | | 1.5 | 1 | .9 | | 3.3 | 4.5 | 5 | 6 | 7 | 1 | 3.7 |
| Benzoic Acid | | | | 1.5 | 1 | | | | | | | | | | | 4 | 1 | 1 | 1.5 | 2.5 | 2 | |
| Tartaric Acid | | 1 | | | 1.5 | 1 | | | | .5 | .5 | .5 | 1 | | | 3 | 2 | 4 | 2.5 | 1.5 | | .3 |

TABLE VII-continued

| COMPONENTS (GRAMS) | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|---|---|---|---|---|---|---|---|---|---|---|---|---|
| Oleic Acid | | | 4 | | | | | | | | | | | | | | | | | | | | | | | | | | | |
| Undecanoic Acid | | | 1 | | | | | | | | | | | | | | | | | | | | | | | | | | | |
| Eicosanoic Acid | | | 1 | 5 | | | | | | | | | | | | | | | | | | | | | | | | | | |
| Dodecanoic Acid | | | 1 | 1 | | | 2 | | | | | | | | | | | | | | | | | .5 | | | | | | |
| Palmitic Acid | | | 1 | | | | | | | | | | | | | | | | | | | | | | | | | | | |
| Stearic Acid | | | 1 | 10 | | | | | | | | | | | | | | | | | | | | | | | 1.5 | | 15 | 12 |
| Arachidic Acid | | | 5 | | | | | | | | | | | | | | | | | | | | | | | | .5 | | | |
| Triacontanoic Acid | | | 1 | | | | | | | | | | | | | | | | | | | 5 | | 2.5 | | | | | | |
| Linoleic Acid | | | | | | | | | | | | | | 1 | | | | | | | | | | 1 | | | | | | |
| Linolenic Acid | | | 9 | | | | | | | | | | | | | | | | | | | | | 2.5 | | | | | | |
| Palm Oil | | | | | | | | | | | | | | | | | | | | | | | | .5 | | | | | 15.5 | |
| Vegetable Oil | | | | | | | | | | | | | | | | | 10 | | | | | | | | | | | | | |
| Coconut Oil | | | | 5 | | | | | | | | | | | | | | | | | 4 | 2 | | | | | | | | |
| Safflower Oil | | 26 | | 10 | 34 | | 33.8 | | | | | | | 6 | | | | | | 5 | 5 | 5 | | 18 | | | | | | 20 |
| Cottonseed Oil | | | | 5 | | | | | | | | | | | | 7.5 | | | | | | | 15 | | | | | | | |
| Sunflower Oil | | | | 1 | | | | | | | | | | | | | | 8.8 | | | | | | | | | | | | |

EXAMPLE NO.

| COMPONENTS (GRAMS) | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|---|---|---|---|---|---|---|---|---|---|---|---|---|
| Lactoglobulin | 43.5 | 46 | 47 | 48 | 49.5 | 42 | 41 | 40 | 59 | 58.5 | 57 | 53 | 54 | 55.5 | 56 | 54.5 | 52 | 42.5 | 46.5 | 50 | 58 | 56 | 41 | 42 | 42.6 | 43 | 44 | 50 | 51.5 | 52 |
| Lactalbumin | 20 | 18 | 17 | 15.5 | 13.5 | 19 | 17.5 | 14.5 | 10.5 | 17.5 | 18 | 19 | 18.3 | 18.2 | 12 | 12.5 | 13 | 15 | 17.5 | 10 | 10 | 10 | 10 | 11 | 12 | 13 | 13 | 10 | 10 | 10 |
| Bacitracin | | | | | | | | | 12 | | | | | | | | | | | 19.3 | 19.3 | 2.3 | 24 | 22 | 19.7 | 18 | 20 | 15.3 | 19 | 18 |
| Selenium | | | | | | | | | .5 | | | | | | | | | | | .7 | .7 | .7 | 1 | 1 | .7 | 1 | 1 | 1 | 1 | 1 |
| Petrolatum U.S.P. | .5 | 1 | .7 | | | | .5 | .6 | | | | | .5 | | .3 | | | | | | | | | 2 | 6 | 3 | 5 | .7 | .5 | |
| Ethanol | 13 | 12 | | 8 | 8 | 7.5 | 8 | 13 | 7.5 | 7 | 7 | 7 | 7 | 7 | 7 | 8 | 9 | 10 | 7.5 | 7 | 7 | 7 | 7 | 7 | | 7 | 7 | 8 | 7 | 8 |
| Lanolin U.S.P. | 1 | 1 | | .5 | | | 1.5 | | | | | | | | | | | | | | | | 5 | 4.5 | .5 | 1 | 1.5 | 1 | 1.5 | |
| Glycerol | 2 | | 1 | | 1.5 | | | | 1 | | | | | | | | | | | | | | | | | | .5 | | .5 | |
| Benzoic Acid | .5 | | 1 | 1 | | 1.5 | | | | | | | | 1 | | 2 | 1 | 1 | | | | | | | | 1 | 1 | | 1 | |
| Tartaric Acid | | 1 | 1 | 2 | 1.5 | | .5 | .9 | .5 | | | | | | .3 | 3 | 5 | | .5 | | | | | | 3.5 | | | 1 | | |
| Oleic Acid | 3 | | .3 | | 1 | | 1.5 | 1 | 5 | 1 | .5 | | .5 | | | 10 | 1 | | 20 | | | .7 | | | | | 1 | 1 | 2 | |
| Eicosanoic Acid | 10 | 5 | 5 | | | 10 | .5 | 5.5 | | 6 | | | .6 | 1 | | 10 | 1 | 1.5 | 2 | | | | 7 | 5 | 1 | 7 | | 1 | | 4 |
| Palmitic Acid | .5 | 5 | 2 | | | | 3 | | | 5 | | | 4 | | | | 1 | 5 | | | | | 5 | 1 | 1 | 1 | 1 | 1 | 1 | |
| Stearic Acid | 15 | 1 | 1 | 10 | | | 11 | | | | | | 5 | 1 | | | 1 | 5 | | 13 | 5 | 6 | | 1 | 2 | 1 | | 1 | 5 | |
| Arachidonic Acid | | 3 | 3 | | | 6 | | | | | | | 2 | 2 | | | | 10 | | | | | | | | | | 1 | | 2 |
| Linoleic Acid | | 1 | 1 | 5 | 5 | 4 | 4 | 9.5 | | | 2.5 | | 2 | 2 | | 10 | | 11 | | | | | 6 | 1 | 2 | 10 | | 4 | 5 | 5 |
| Palm Oil | | 2 | 1 | | | | | | | | | | 2 | | 3 | | 4 | 10 | | | | | 6 | | | | | | | |
| Vegetable Oil | | | 10 | 10 | 10 | 10 | 5 | 5 | 4 | | | 21 | 2 | | | | 1 | | | | | | | | | | 2 | | | 2 |
| Coconut Oil | | 2 | | | 4 | | 5 | | | 5 | 15 | | | 10 | 1.2 | | | | | | 5 | | | | | | | | | 5 |
| Safflower Oil | | 4 | | | 5 | | | | | | | | | | .5 | | | | | | | | | | | | 7 | | | |
| Cottonseed Oil | | | | | | | | | | | | | | | 11 | | | | | | | | | | | | | 5 | | |
| Sunflower Oil | | | | | | | | 10 | | | | | | | | | | | | | | | | | | | | | | |
| B-caroten-3-ol | 1 | | 1 | | | | | | | | | | | | | | | | | | | | | | | | | | | |

EXAMPLE NO.

| COMPONENTS (GRAMS) | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 |
|---|---|---|---|---|---|---|---|---|---|---|---|---|---|---|---|---|---|---|---|---|---|---|---|---|---|---|---|---|
| Lactoglobulin | 41 | 41 | 41 | 41 | 41 | 42 | 42 | 42 | 42 | 43 | 43 | 43 | 43 | 43 | 45 | 45 | 45 | 45 | 46 | 46 | 46 | 46 | 47 | 47 | 58 | 57 | 56 | 55 |
| Lactalbumin | 20 | 19 | 18 | 17 | 16 | 20 | 19 | 18 | 17 | 16 | 16 | 15 | 18 | 19 | 15 | 14 | 13 | 12 | 11 | 12 | 13 | 14 | 13 | 12 | 10 | 11 | 12 | 15 |
| Bacitracin | 11.5 | 12 | 11.5 | 12.4 | 11.5 | 11.5 | 11.4 | | | 11.5 | 11.5 | 11.5 | 11.5 | | | | | | | | | | | | | 11.5 | 12.3 | |
| Selenium | .5 | .5 | .5 | .6 | .5 | .5 | .6 | | 1 | .5 | .5 | .5 | .5 | 1 | 2 | | | 3 | | 1 | | 2 | | 1 | | .5 | .7 | |
| Petrolatum U.S.P. | | 1 | 1 | 1 | 2 | 2 | 2 | | | 1 | 1 | 1 | | | | | | | | | | | | | | 3 | | |

TABLE VII-continued

| COMPONENTS (GRAMS) | | | | | | | | | | | | | | | | |
|---|---|---|---|---|---|---|---|---|---|---|---|---|---|---|---|---|
| Ethanol | | | | | | 1 | 1 | | | | | | | | | |
| Lanolin U.S.P. | 15 | 14 | 13 | 12 | 7 | 8 | 10 | 8 | 7 | 8 | 7 | 11 | 7 | 7 | 8 | 7 |
| Glycerol | 2 | 5 | 10 | 1 | 7 | 1 | 1 | 7 | 1 | 7 | 1 | | 1 | 2 | 1 | |
| Benzoic Acid | 3 | | | 3.5 | | 5 | 5 | 5 | 4 | | 2 | | | | | |
| Tartaric Acid | | 1 | | .5 | | | | | 4.5 | | | | | | | |
| Oleic Acid | | | | | | | | | | | | | | | | |
| Eicosanoic Acid | | 1 | 1 | 1 | | 10 | 10 | 9 | | | | | | | | |
| Palmitic Acid | | | 1 | | | | | | | | | | | | | |
| Stearic Acid | 2.5 | 1 | | | | 15 | 5 | | | | 5 | 15 | 30 | 31 | 31 | 25 |
| Arachidonic Acid | | 1 | | | | | 5 | 2 | | | | | | | | |
| Linoleic Acid | 1.5 | | | | | | | 13 | | | | | | | | |
| Palm Oil | 3 | | | | | | 5 | | 1 | | | | | | | |
| Vegetable Oil | | | | | | | | | | | | | | | | |
| Coconut Oil | 1 | 5 | | | 10 | 10 | | | | 15 | | | | | | |
| Safflower Oil | 1 | | | | | | | | | | 10 | | | | | |
| Sesame Oil | 1 | | | | | | | | 24 | 15 | | | | | | |
| Cottonseed Oil | .2 | | 5 | | | | | | | | | | | | | |
| Sunflower Oil | 5 | | | | | | | | | | | 15 | | | | |
| B-caroten-3-ol | | | | | | | | | | | | | | | | 10 12 23 |
| pentyl-B-caroten-ol | | | | | 1 | | | | | | | | | | | |
| decyl-B-caroten-3-ol | | | | | 1 | | | | 1 | 1 | 2 | | | | | |
| Tocopherol | | | | | 5 | | 1 | 5 | | 3 | 2 | | | | | |

| | EXAMPLE NO. | | | | | | | | | | | | | | | | | |
|---|---|---|---|---|---|---|---|---|---|---|---|---|---|---|---|---|---|---|
| | 110 | 111 | 112 | 113 | 114 | 115 | 116 | 117 | 118 | 119 | 120 | 121 | 122 | 123 | 124 | 125 | 126 | 127 |
| Lactoglobulin | 55 | 56 | 57 | 58 | 59 | 60 | 54 | 53 | 52 | 40 | 41 | 42 | 43 | 44 | 40 | 41 | 42 | 42 |
| Lactalbumin | | | | | | | | | | 10 | 11 | 10 | 11 | 12 | 1.5 | 10 | 11 | 10 |
| Bacitracin | | | | | | | | | | | | 11.3 | 11.5 | | 24 | 23 | 22 | 21 |
| Selenium | | | | | | | | | | | | .7 | .5 | | 1 | 1 | 1 | 1 |
| Pertrolatum U.S.P. | | | | | | | | | | | | 2.5 | | 3 | | | | 1 |
| Ethanol (40%) | 1 | 1.5 | 7.6 | 8 | .5 | .6 | .7 | .9 | | 1 | 2 | 1 | 3 | | 8 | 8.4 | 8.5 | 9 |
| Lanolin U.S.P. | 7 | 7.5 | | | 10 | 8.5 | 7.3 | 7.1 | 13 | 15 | 8.6 | 9 | 9.5 | 13.2 | 10 | 9 | 8 | 7 |
| Gylcerol | | | 1 | 2 | 3 | 4 | 5 | | | 4 | 5 | 6 | 7 | 8 | | | | 2.3 |
| Benzoic Acid | .5 | | | | | | | | | 1 | | | 2 | | .5 | | 1 | 3.2 |
| Tartaric Acid | 1 | | 1.1 | | | 1 | 1 | 1 | | .5 | 2 | 3 | 1 | | 1 | 6.5 | 2.2 | |
| Oleic Acid | | | 29 | 29.6 | | 35 | | | | 1.5 | | 4.5 | .5 | 5.3 | 5 | | 4.3 | |
| Palmitic Acid | | | | | | | | | | 2 | | 10 | 5 | .5 | | | | |
| Stearic Acid | | | | | | | | | | 15 | | | | | | | | 3.5 |
| Arachidonic Acid | | | | | | | | | | | | | | 3 | | | | |
| Palm Oil | | | | | | | | | | | | | | | | | | |
| Coconut Oil | | | | | | | | | | | | | | | | | | |
| Safflower Oil | | | | | | | | | | | | | 5 | | | | | |
| Sesame Oil | | | | | | | | | | | | | | | | | | |
| Cottonseed Oil | | | | | | | | | | | | | | | | | | |
| Sunflower Oil | | | | | | | | | | | | | | | | | | |
| Tocopherol | .1 | 12 | | | | | | | | | | | | | | | | |
| Soybean Oil | | .2 | | | | | .5 | .6 | .7 | | | | | | | | | |
| Olive Oil | 1 | 1 | 1 | | 1 | 1 | 1 | 1 | 1 | | | | | | | | | |
| Peanut Oil | | | | | | 1 | | | | | | | | | | | | |
| Rice Oil | | | | | | 35 | 29 | 35 | | | 10 | | | 10 | | | | |
| Corn Oil | | | | | | | | | | | 10 | | | | | | | |
| Wheatgerm Oil | 1 | 1.1 | 1.2 | 1.3 | 1.4 | 1.5 | 1.6 | 1.7 | 1.8 | | 9 | | | | | | | |

TABLE VII-continued

| COMPONENTS (GRAMS) | 128 | 129 | 130 | 131 | 132 | 133 | 134 | 135 | 136 | 137 | 138 | 139 | 140 | 141 | 142 | 143 | 144 | 145 |
|---|---|---|---|---|---|---|---|---|---|---|---|---|---|---|---|---|---|---|
| Myristic Oil | 22.4 | 2.7 | | | | | .9 | .7 | 21.5 | | .4 | | | | | | | |
| | | | | | | | | | EXAMPLE NO. | | | | | | | | | |
| Lactoglobulin | 43 | 43 | 44 | 45 | 46 | 47 | 48 | 40 | 41 | 42 | 42 | 41 | 43 | 43.5 | 44 | 50 | 55 | 60 |
| Lactalbumin | 11 | 12 | 13 | 10 | 11 | 12 | 13 | 11 | 12 | 11 | 10 | 13 | 14 | 15 | 10 | 10 | 10 | 10 |
| Bacitracin | 19 | 18 | 20 | 19.8 | 17.8 | 19 | 11.4 | 11.4 | 12.4 | 11.8 | 13.5 | 14.5 | 13 | 12.4 | 13.5 | 14.4 | 11.5 | 11.5 |
| Selenium | 1 | 1 | 1 | .7 | .7 | 1 | .6 | .6 | .6 | .7 | .5 | .5 | .5 | .6 | .5 | .6 | .5 | .6 |
| Petrolatum U.S.P. | | | | | | | | 2.5 | 1.5 | | | | | 1 | | | | |
| Ethanol (40%) | | | | | | | | 1 | 1.2 | 1.3 | 1.4 | | | | | | | |
| Lanolin U.S.P. | 0.5 | 10 | 1.5 | 11 | 11.5 | 12 | 12.5 | 13 | 14 | 15 | 16 | 17 | 18 | 19 | 20 | 10 | 10 | 11 |
| Glycerol | 6 | 5 | 4.5 | 8.5 | 7.3 | | | | 1 | 2 | 3 | 4 | 5 | 6 | 5 | 5.5 | | |
| Benzoic Acid | | 1 | | | | | 1 | | 1 | | 1 | | | | | | | |
| Tartaric Acid | | 2 | | | | | 1.2 | | | | | 1.3 | 1.4 | 1.5 | 1.6 | .5 | | |
| Oleic Acid | .5 | 5 | | | 2.7 | | 2.3 | .5 | 1.5 | 1.2 | 1.2 | .7 | 1.1 | .1 | .4 | .5 | 3 | 1 |
| Palmitic Acid | 2 | 2 | | | | | 1 | 1 | .8 | | | 1.5 | | .1 | .1 | .5 | 3 | 1 |
| Stearic Acid | 2 | | | | | 8 | | 1 | 1 | 1.2 | | | .2 | | .1 | .5 | 3 | 1 |
| Arachidonic Acid | 2 | | | | | | | 1 | 1 | 1 | | .5 | .2 | .1 | .1 | .5 | 1 | 1 |
| Palm Oil | 2 | | | | | | | 1 | 1 | 1 | | .5 | .2 | .1 | .1 | .5 | | 1 |
| Coconut Oil | | | 6 | | | | | 1 | 1 | 1 | .5 | .5 | .2 | .1 | .2 | .5 | | .1 |
| Safflower Oil | | | | 5 | | | | 1 | 1 | 1 | .3 | .5 | .2 | .1 | .2 | .5 | | .1 |
| Sesame Oil | | | | | | | | 1 | 1 | 1 | | .5 | .2 | .1 | .1 | 1.5 | | .1 |
| Cottonseed Oil | | | | | | | | 1 | 1 | 1 | .5 | | .2 | | | 1.5 | | .1 |
| Sunflower Oil | | | | | | | | 1 | 1 | 1 | .5 | | .5 | | 1 | 1.5 | | .1 |
| Tocopherol | | | | | | | | | | | .5 | | .5 | | 1 | 1.5 | | .1 |
| Soybean Oil | | | | | | | | | | | 2 | | | | | 1.5 | | .1 |
| Olive Oil | | | | | | | | | | | 2 | | | | | 1.5 | | .1 |
| Peanut Oil | | | | | | | | | | | 2 | | | | | 1.5 | | .1 |
| Rice Oil | | | | | | | | 4 | | | 1.1 | | 1 | | | 1.5 | | .1 |
| Corn Oil | | | | | | | | 1 | | 1.1 | | | | | | 3 | | .1 |
| Wheatgerm Oil | | | | | | 3 | | | | | | | | | | | | |
| Myristic Oil | | | | | | | | | | | | | | | | | | |

| COMPONENTS (GRAMS) | 146 | 147 | 148 | 149 | 150 | 151 | 152 | 153 | 154 | 155 | 156 | 157 | 158 | 159 | 160 | 161 |
|---|---|---|---|---|---|---|---|---|---|---|---|---|---|---|---|---|
| | | | | | | | | EXAMPLE NO. | | | | | | | | |
| Lactoglobulin | 4.5 | 41.5 | 42.5 | 43.5 | 44 | 44.5 | 46 | 47 | 48 | 49 | 50 | 51 | 41 | 42 | 43 | 44 |
| Lactalbumin | 10 | 1.5 | 11 | 11.5 | 12 | 12.5 | 1.7 | 11.3 | 12.3 | 12 | 10 | 10 | 1.2 | 1.4 | 1.6 | 11 |
| Bacitracin | 24 | 23.5 | 23 | 22 | 21.5 | 21 | 20 | 21 | 22 | 2.4 | 19 | 15.2 | 24 | 23.6 | 23.6 | 22 |
| Selenium | 1 | 1 | 1 | 1 | 1 | 1 | 1 | .7 | .7 | .9 | 1 | .8 | .8 | 1 | .8 | 1 |
| Petrolatum U.S.P. | .5 | .5 | .5 | | | 1 | .3 | | | 2 | | | | | | |
| Ethanol (70%) | | | | | | 1 | | | | | | | | | | |
| Lanolin U.S.P.* | 13 | 12 | 11 | 10 | 9 | 8 | 7 | 2 | 7.2 | 7.3 | 7 | 7 | 8.2 | 8.4 | 8 | 7.5 |
| Glycerol (5% H₂O) | | 1 | .5 | .7 | .8 | .9 | 7 | 7 | .4 | 3 | | 1 | 5 | 5 | 4 | 3 |
| Benzioc Acid | .3 | .2 | .4 | .5 | | | 1 | .2 | | | | | 1 | 3 | 2 | 1 |
| Tartaric Acid | .2 | .3 | .6 | .5 | | | | | | | | | 3 | 1 | 2 | 1 |
| Oleic Acid | .5 | 8.5 | .5 | | .7 | 1.1 | | .8 | .4 | .4 | | | | | | |
| Palmitic Acid | | | 9 | 9 | 1 | | | | | | | | .8 | .6 | | .5 |
| Stearic Acid | 10 | | | .3 | 10 | | | | | | 3 | 5 | 6 | 5 | | |
| Eicosatrienoic Acid | | | | | | 4 | | | | | | | | | | |
| Arachidonic Acid | | | | | | | | | | | | | | | 6 | |
| Palm Oil | | | | | | | | | | | | | | | | |

TABLE VII-continued

| COMPONENTS (GRAMS) | 162 | 163 | 164 | 165 | 166 | 167 | 168 | 169 | 170 | 171 | 172 | 173 | 174 | 175 | 176 |
|---|---|---|---|---|---|---|---|---|---|---|---|---|---|---|---|
| Coconut Oil | | | | | | | | | | | | | | | |
| Safflower Oil | | | | | | | | | | | | | | | |
| Sesame Oil | | | | | | | | | | | | | | | |
| Cottonseed Oil | | | | | | 5 | | | | | | | | | |
| Sunflower Oil | | | | | | | | | | | 10 | | | | |
| Tocopherol | | | | | | | | | | | | | | | |
| Soybean Oil | | | | | | | 9 | | | | | | | | |
| Olive Oil | | | | | | | | | | | | | | | |
| Peanut Oil | | | | | | | | | | | | | | | |
| Rice Oil | | | | | | | | | | | | | | | |
| Wheatgerm Oil | | | | | | | | | | 10 | | | | | 9 |
| Myristic Acid | | | | | | | | | | | | | | | |

EXAMPLE NO.

| | 162 | 163 | 164 | 165 | 166 | 167 | 168 | 169 | 170 | 171 | 172 | 173 | 174 | 175 | 176 |
|---|---|---|---|---|---|---|---|---|---|---|---|---|---|---|---|
| Lactoglobulin | 45 | 46 | 40 | 40 | 40 | 41 | 42 | 43 | 44 | 45 | 46 | 47 | 48 | 49 | 50 |
| Lactalbumin | 12.2 | 11.4 | 19 | 20 | 20 | 19 | 18 | 17 | 17.5 | 16.5 | 16 | 15.5 | 14.5 | 13.6 | 14.2 |
| Bacitracin | 21 | 19.8 | 22 | 11.5 | 11.8 | 12.5 | 13.4 | 14.5 | 13.3 | 12.5 | 11.5 | 11.5 | 12.5 | 13.4 | 13.1 |
| Selenium | 1 | .8 | 1 | .5 | .7 | .5 | .6 | .5 | .7 | .5 | .5 | .5 | .5 | .6 | .7 |
| Petrolatum U.S.P. | 1 | | 1 | | .5 | 1 | 1.5 | 2 | 2.5 | 3 | 2 | 1 | | | |
| Ethanol (70%) | 7 | 7 | 12 | 12.6 | 12.4 | 12 | 11.5 | 10 | 9.5 | 9 | 8.5 | 8 | 7 | 7 | 7 |
| Lanolin U.S.P.* | 1 | 1.5 | 1.8 | 1 | 1 | 1 | 1 | 1 | 1.2 | 1.4 | 1.5 | 2 | | | |
| Glycerol (5% H$_2$O) | 1.5 | | | | .6 | | | | | | | | | | |
| Benzoic Acid | 1.5 | | | | 1 | | | | | | | | | .4 | |
| Tartaric Acid | .8 | 2.5 | 3.2 | | | | | | | | | | | | |
| Oleic Acid | | 10 | | 14 | | | | | | | | | | | |
| Palmitic Acid | | | | | | | | | | | | | | | |
| Stearic Acid | | | | | | | | | | | | | | | |
| Eicosatrienoic Acid | | | | | | | | | | | | | | | |
| Arachidonic Acid | | | | | | | | | | | | | | | |
| Palm Oil | | | | | | | | | | | | | | | |
| Coconut Oil | 8 | | | | | | | | | | | | | | |
| Safflower Oil | | | | | | | | | | | | | | | |
| Sesame Oil | | | | | | | | | | | | | | | |
| Cottonseed Oil | | | | | | | | | | | | | | | |
| Sunflower Oil | | | | | | | | | | | | | | | |
| Tocopherol | | | | | | | | | | 1.1 | | | | | |
| Soybean Oil | | | | | | | | | | 11 | 11 | | 1 | 2 | 1 |
| Olive Oil | | | | | | | | | .3 | | 3 | | 1 | | |
| Peanut Oil | | | | | | | | | 11 | | | | | | |
| Rice Oil | | | | | | | | | | | | | 1 | | |
| Wheatgerm Oil | | | | | | | | | | | | 14 | | 14 | 14 |
| Myristic Acid | | | | | | | | | | | | .5 | 13 | | |

| | 177 | 178 | 179 | 180 | 181 | 182 | 183 | 184 | 185 | 186 | 187 | 188 | 189 | 190 | 191 | 192 |
|---|---|---|---|---|---|---|---|---|---|---|---|---|---|---|---|---|
| Lactoglobulin | 60 | 59 | 58 | 58 | 53 | 49 | 49 | 56 | 57 | 57 | 56 | 55 | 54 | 53 | 52 | 46 |
| Lactalbumin | | | | | 20 | 20 | 19 | 18 | 17 | 16 | 15 | 16 | 17.5 | 20 | 19 | 18 |
| Bacitracin | | | | | 11.5 | 11.5 | 12.3 | 11.3 | 11.5 | 12.5 | 13.3 | 12 | 12 | 11.5 | 11.5 | 11.5 |
| Selenium | | | | | .5 | | .7 | .7 | .5 | .5 | .7 | .5 | .5 | .5 | .5 | .5 |
| Petrolatum U.S.P. | | | | | .5 | | | .5 | | .5 | 1 | 1 | | .5 | 1 | 1 |

TABLE VII-continued

| COMPONENTS (GRAMS) | 193 | 194 | 195 | 196 | 197 | 198 | 199 | 200 | 201 | 202 | 203 | 204 | 205 | 206 | 207 | 208 |
|---|---|---|---|---|---|---|---|---|---|---|---|---|---|---|---|---|
| Ethanol (80%) | .5 | 1 | 1 | 1 | 1 | 1 | 1 | 1 | 1 | 1 | 1 | 1 | 1 | 1 | 1 | 1 |
| Lanolin U.S.P.* | 7 | 7 | 7 | 7 | 7 | 7 | 7.5 | 7 | 8 | 8.3 | 8.4 | 9 | 7.5 | 9 | 13 | 8 |
| Glycerol (10% H$_2$O) |  |  |  |  |  |  | 7 | 7 | 1 | .5 | 1 | 1 | .7 | 1 | 1 | 1.2 |
| Benzoic Acid |  |  |  |  |  |  | 1.4 | 1.3 |  |  |  |  | .7 | .8 |  | 1.1 |
| Tartaric Acid |  | 5 |  | 2 |  | 1.2 |  |  |  |  |  |  | .8 |  |  | 1.5 |
| Oleic Acid |  | 3 | 4 | 3 | .4 |  |  |  |  | .5 | .3 |  | .2 |  |  | 1.2 |
| Palmitic Acid | .5 |  |  | 1 | .1 |  | 1.1 |  |  |  | .7 |  | .3 |  |  |  |
| Stearic Acid | 22 | 20 | 30 | 3 | 4 | .8 | 1 |  |  | .5 | .3 | .1 | 1 |  | .1 |  |
| Eicosatrienoic Acid | 10 | 5 |  | 25 |  | 1 | 1 |  | .2 | .5 | .2 | 1 | 1 | 1 | 1 |  |
| Arachidonic Acid |  |  |  |  |  | 1 | 2 |  | .2 | .5 | .5 | 1 | 1 | 1 | .1 | 1 |
| Palm Oil |  |  |  |  |  | 1 | 2 |  | .2 | .5 | .1 |  |  | .2 | .1 |  |
| Coconut Oil** |  |  |  |  |  |  | 2 |  | .2 |  | .1 |  |  | 1 | .1 |  |
| Safflower Oil |  |  |  |  | 4 | .5 |  |  | .2 |  | .1 |  |  | 1 | .1 | 1 |
| Sesame Oil |  |  |  |  |  | .5 |  |  | .2 |  | .1 |  |  | 1 | .1 | 1 |
| Cottonseed Oil*** |  |  |  |  |  |  |  |  | .5 |  | .4 |  |  |  |  | 1 |
| Sunflower Oil |  |  |  |  |  |  |  |  | .5 |  |  |  |  |  |  |  |
| Soybean Oil |  |  |  |  |  |  |  | 1 | .5 |  | 1.5 |  |  |  |  |  |
| Olive Oil |  |  |  |  |  |  |  | 1 | .5 |  |  |  |  |  |  |  |
| Peanut Oil |  |  |  |  |  |  |  |  |  |  |  |  |  |  |  |  |
| Rice Oil |  |  |  |  |  |  |  |  |  |  |  |  |  |  |  |  |
| Wheatgerm Oil** |  |  |  |  |  |  |  |  |  |  |  |  |  |  |  |  |
| Myristic Acid |  |  |  |  |  |  |  |  |  |  |  |  |  |  |  |  |

| | EXAMPLE NO. | | | | | | | | | | | | | | | |
|---|---|---|---|---|---|---|---|---|---|---|---|---|---|---|---|---|
| | 193 | 194 | 195 | 196 | 197 | 198 | 199 | 200 | 201 | 202 | 203 | 204 | 205 | 206 | 207 | 208 |
| Lactoglobulin | 50 | 49 | 48 | 45 | 40 | 45 | 43 | 42 | 46 | 47 | 50 | 52 | 53 | 54 | 55 | 60 |
| Lactalbumin |  | 15 | 16 | 17 | 12 | 12.5 | 13 | 12 | 14 | 15 | 12.5 | 13 | 14 | 15 | 16 | 12 |
| Bacitracin |  | .5 |  |  | 11.4 | 12.4 | 13.4 | 11.4 | 12.4 | 13.4 | 14.5 | 14 | 14.3 | 14.3 | 14.3 | 14.5 |
| Selenium |  |  |  | .3 | .6 | .6 | .6 | .6 | .6 | .6 | .5 | .7 | .7 | .7 |  |  |
| Petrolatum U.S.P. |  |  | .7 |  | .5 |  |  | .8 | .9 |  | .5 | 1.2 | 1.3 | 1.4 | .5 |  |
| Ethanol (80%) | 1 |  |  | 2 | 1 | 1 | 1 | 1 | 1 | 1 | 1.1 | 1 | 1 | 1 | 1.5 |  |
| Lanolin U.S.P.* | 14 |  |  | 35 | 7.1 | 7.2 | 7.3 | 2.5 | 1.7 | 1.2 |  | 9 | 7 | 7 | 7 | 7 |
| Glycerol (10% H$_2$O) | 1.2 | 35 |  | 2.7 |  |  | 3 | 7.4 | 7.5 | 7.6 | 8 | 2.2 | 2 | 2 | 2 | 2 |
| Benzoic Acid |  |  |  |  |  |  |  | 2 | 2.5 | 4 | 2 | .1 |  |  |  |  |
| Tartaric Acid | .8 |  |  |  |  |  |  |  | .4 |  |  | 3.5 |  |  |  |  |
| Oleic Acid | 30 |  |  |  | .4 | .7 | 1 | .3 |  | .2 | .4 | .5 |  | .6 |  |  |
| Palmitic Acid | 7 |  |  |  |  |  |  |  | 1 | .5 |  | 1 | .5 | .5 | .5 | .1 |
| Stearic Acid |  |  |  |  |  | 1 | 1 | 1 | 1 | .5 | 1 |  | .5 | .5 |  | .1 |
| Eicosatrienoic Acid |  |  | .3 |  |  | 1 | 1 | 1 | 1 | .5 | 1 | 1 | .5 | .5 |  | .1 |
| Arachidonic Acid |  |  |  | .7 |  | 1 | 1 | 1 | 1 | 1 | 1 | 1 | .5 | .5 |  | .1 |
| Palm Oil |  |  |  | 2 |  | 2 | 1 | 1 | 1 | 1 | 2 | 1 | .5 | 1 |  | .5 |
| Coconut Oil** |  |  |  | 35 | 2 | 1 | 1 | 1 | 1 | 2 | 2 |  | 1 |  |  |  |
| Safflower Oil |  |  |  |  | .3 | 2 | 1 | 1 | 1 | 1 | 1 | .5 | .5 |  |  |  |
| Sesame Oil |  |  |  |  | 5 | 2 | 1 | 1 | 1 | 1 |  | 1 | .5 |  |  |  |
| Cottonseed Oil*** |  |  |  |  | 5 | 2 | 1 | 1 | 1 |  |  |  | .5 |  |  |  |
| Sunflower Oil |  |  |  |  | 5 | 2 | 1 | 1 | 1 |  |  |  | .5 |  |  |  |
| Soybean Oil |  |  | 35 |  | 4 | 2 | 1 | 1 | 1 |  |  |  | .5 |  |  |  |
| Olive Oil |  |  |  |  |  |  | 1 | 1 | 1 |  |  |  |  |  | 1 |  |
| Peanut Oil |  |  |  |  |  |  |  |  |  |  |  |  |  |  |  |  |
| Rice Oil |  |  |  |  |  |  | 1 | 1 | 1 |  |  |  |  |  | 1 | 1 |
| Wheatgerm Oil** |  |  |  |  |  |  | 1 | 1 | 1 |  |  |  |  |  |  | 1 |

TABLE VII-continued

| COMPONENTS (GRAMS) | EXAMPLE NO. | | | | | | | | | | | | | | |
|---|---|---|---|---|---|---|---|---|---|---|---|---|---|---|---|
| | 209 | 210 | 211 | 212 | 213 | 214 | 215 | 216 | 217 | 218 | 219 | 220 | 221 | 222 | 223 |
| Lactoglobulin****** | 40 | 41 | 42 | 43 | 44 | 45 | 46 | 47 | 48 | 47 | 46 | 45 | 44 | 50 | 51 |
| Lactalbumin***** | 10 | 11 | 17 | 18 | 19 | 10 | 11.6 | 11.7 | 12 | 13 | 12 | 14 | 15 | 10 | 11 |
| Bacitracin | 24 | 23 | 22 | 21 | 22.7 | 19 | 14.3 | 15.2 | 16.2 | 17 | 18 | 19 | 18.2 | 11.5 | |
| Selenium | 1 | 1 | 1 | 1 | .8 | 1 | .7 | .8 | .8 | 1 | 1 | 1 | .8 | .5 | |
| Petrolatum U.S.P. | 6 | 3.5 | 3 | | | | | 1 | 1 | 1 | 3 | | | | |
| Ethanol (50%) | 1 | 1 | 1 | 1 | | | | | | | .5 | | | .7 | |
| Lanolin U.S.P.* | 7.2 | 7.5 | 8 | 8.5 | 9 | 8 | 7.4 | 13.3 | 12 | 11 | 7 | 15 | 17 | 10 | 10 |
| Gylcerol (15% H₂O) | .5 | 2 | 1.5 | 1 | 1.2 | 2.5 | 3 | | | 1.2 | 1.3 | 1.4 | 1.5 | 1 | |
| Benzoic Acid***** | | 1 | .5 | | 1 | | | | | .3 | .2 | | .5 | .8 | 1 |
| Meso-Tartaric Acid | .5 | 1 | 1 | 1 | .5 | 1 | 2 | 3 | 1 | 1 | | | | | |
| Oleic Acid | | | | | | | | | | | | | 3 | 1 | 10 |
| Palmitic Acid | | | | | | | | | | | | | | | 10 |
| Stearic Acid | | | | | | | | | | | | | | | 5 |
| Eicosatrienoic Acid | | | | | | | | | | | | | | | |
| Arachidonic Acid | | | | | | | | | | | | | | | |
| Palm Oil** | | | | | | | | | | | | | | | |
| Coconut Oil** | | | | | | | | | | | | | | | |
| Safflower Oil | | | | 5 | | | | | | | | | | | |
| Sesame Oil | | | | | | | | | | | | | | | |
| Cottonseed Oil**** | | | | | | | | | | | 10 | | | | |
| Sunflower Oil | | | | | | | | | | | | 4.6 | | | |
| Soybean Oil** | | | | | | | | | 9 | | | | | | |
| Olive Oil | | | | | | | | | | 7 | | | | | |
| Peanut Oil** | 8 | | | .5 | .8 | | | | | | | | | | |
| Rice Oil | 1.8 | | | | | 3 | 15 | 8 | | | | | | | |
| Wheatgerm Oil** | | .5 | 3 | | | .5 | | | | | 1 | | | | 2 |
| Myristic Acid | | | | | | | | | | | | | | | |

| COMPONENTS (GRAMS) | EXAMPLE NO. | | | | | | | | | | | | | | |
|---|---|---|---|---|---|---|---|---|---|---|---|---|---|---|---|
| | 224 | 225 | 226 | 227 | 228 | 229 | 230 | 231 | 232 | 233 | 234 | 235 | 236 | 237 | 238 |
| Lactoglobulin****** | 52 | 53 | 54 | 54 | 55 | 56 | 56 | 57 | 58 | 59 | 60 | 45 | 50 | 55 | 51 |
| Lactalbumin***** | 12 | 13 | 14 | 15 | 10 | 11 | 10 | 10 | 1.5 | 12 | 13 | 12 | 11 | 12 | 11 |
| Batcitracin | | | | | 16.3 | | | | 11.4 | 12 | 12.5 | 13 | 13.4 | 13.5 | 12.4 |
| Selenium | | | | | .7 | | | | .6 | .5 | .5 | .5 | .6 | .5 | .6 |
| Petrolatum U.S.P. | | | | 1 | 2 | | | 1 | | | | | | | |
| Ethanol (50%) | | | | | .9 | | | 7 | 7 | | .5 | | .7 | | |
| Lanolin U.S.P.* | 10 | 9 | 8 | 8 | 7 | 7 | 7 | 7 | 7 | 7 | 7 | 15 | 10 | 8 | 8 |
| Gylcerol (15% H₂O) | | | | | | | .3 | 1 | 1 | | | | | | |
| Benzoic Acid***** | 1 | 1 | | | | .3 | .7 | 4 | .5 | .5 | 1 | | .9 | | |
| Meso-Tartaric Acid | | | | .5 | .6 | .7 | | | | | | | .1 | | |
| Oleic Acid | | | | | 2 | 5 | 5 | 10 | 3 | | | 2 | .3 | | |
| Palmitic Acid | | | | | 2 | 10 | 4 | 2 | 2 | | | | | | |
| Stearic Acid | | 10 | | | 2 | 5 | 1 | 2 | 2 | | | | | | |
| Eicosatrienoic Acid | | 1 | | | | | | | 2 | | | | | | |
| Arachidonic Acid | | 1 | | | | | | | 1 | | | | | | |
| Palm Oil** | | 1 | | | | | | | | | | | | | |
| Coconut Oil** | | | | | | | | | | | | | | | |

TABLE VII-continued

| COMPONENTS (GRAMS) | | | | | | | | | | |
|---|---|---|---|---|---|---|---|---|---|---|
| Safflower Oil | | | | | | | 1 | | | |
| Sesame Oil | | | | | | | 1 | | | |
| Cottonseed Oil***** | | | 5 | | | | 1 | | 2 | |
| Sunflower Oil | 5 | | 4 | | | | 1 | 1.5 | 3 | |
| Soybean Oil** | 5 | | 1 | | | | 1 | | | |
| Olive Oil | | | | | | | 1 | | | |
| Peanut Oil** | | 5 | | | | | 1 | | | |
| Rice Oil | | 4 | | 10 | | | 1 | | | |
| Wheatgerm Oil** | | 10 | | | | | 6 | | | |
| Myristic Acid | 10 | | | 1.5 | | | | | | |

| | EXAMPLE NO. | | | | | | | | | | | | | | | | | | | | | |
|---|---|---|---|---|---|---|---|---|---|---|---|---|---|---|---|---|---|---|---|---|---|---|
| | 239 | 240 | 241 | 242 | 243 | 244 | 245 | 246 | 247 | 248 | 249 | 250 | 251 | 252 | 253 | 254 | 255 | 256 | 257 | 258 | 259 | 260 |
| Lactoglobulin | 60 | 55 | 50 | 45 | 40 | 41 | 43 | 45 | 47 | 49 | 51 | 53 | 54 | 55 | 57 | 59 | 60 | 58 | 56 | 54 | 52 | 50 |
| Lactalbumin (anhydrous) | 10 | 10 | 10 | 11 | 10 | 12 | 13 | 15 | 10 | 13 | 15 | 13.5 | | | | 20 | 18 | 16 | 10 | 11 | 12 | 13 |
| Bacitracin | 16 | 19.2 | 15.2 | 16.2 | 24 | 17.2 | 16.2 | 15.7 | 19 | 20 | 20 | | | | | | | | 11.5 | 12.3 | 11.8 | 13.5 |
| Selenium | 1 | .8 | .8 | .8 | 1 | .8 | .8 | .8 | 1 | 1 | 1 | | | | | | | | .5 | .7 | .7 | .5 |
| Petrolatum U.S.P. (heavy) | | | 1 | 5 | | | 1 | | | | | | | 4 | | | | 2 | | | 1 | |
| Petrolatum U.S.P. (medium) | | | | 4 | | | 1 | | | | | | | 1 | | | | 2 | | | 1 | |
| Ethanol (50%) | | | 1 | 1 | | | 1 | | | | | 10 | | 2 | | | | | | | | |
| Glycerol (50% H2O) | | | 1 | 3 | | | 1 | | | | | | | | | | | .2 | | | .5 | |
| 2,5 Dihydroxybenzoic Acid | | | 1 | 1 | | | | | | | | | | | | | | | | | | |
| Para-Tartaric Acid | | | 1 | 1 | | | | | | | | | | | | | | | | | | |
| Oleic Acid | | | 11 | 4 | | | 5 | | | | | | | | | | | | | | | |
| Elaidic Acid | .6 | | | | | | | | | | | | | | | | | .5 | | | | |
| Palmitic Acid | .4 | | | | 4 | | | | | | | | | | | | | .5 | | | | |
| Palm Oil*** | 5 | | | | 1 | | | | | | | | | | | | | .3 | | | | |
| Coconut Oil**** | | | | | | | | | | | | | 26 | 20 | 16 | | | | | | | |
| Safflower Oil | | 5 | | | | | | 10 | | 7 | 6 | 3 | | | 10 | | | | | | | |
| Sesame Oil | | | | | | 7 | | | | | | | | | | | | | | | | |
| Cottonseed Oil | | | | | | | | | 10 | | | | | | | | | | | | | |
| Olive Oil** | | | | | | | | | | | | | | | | | | | 15 | 14 | | |
| Peanut Oil** | | | | | | | | | | | | | | | | | 1 | .5 | | | | |
| Rice Oil** | | | | | | | | | | | | | | | | | | .5 | | | | 13 |
| Adenosine | | 1 | | | | 2 | | | | | | | | | | 1 | 1 | .5 | | | 1 | 2 |
| Thiophene-3-Carboxylic Acid | | 1 | | | | 1 | | | | | | 1 | | | | 1 | 2 | | | .5 | | |
| Lanolin U.S.P. (5% hydrous) | 7 | 8 | 7 | 8 | 20 | 19 | 18 | 13.5 | 13 | 20 | 7 | 20 | 20 | 18 | 17 | 10 | 12 | 20 | 7 | 7.5 | 8 | 8 |

*hydrous
**hydrogenated
***partially hydrogenated (30% by weight)
****partially hydrogenated (35% by weight)
*****1,3 dihydroxybenzoic acid
******anhydrous From the foregoing, it will be appreciated that the present invention provides multiprotein compounds including beta-lactoglobulin, alpha-lactalbumin, and bacitracin which are useful and effective in the treatment of such medical disorders as psoriasis, arthritis, erythropoietic protoporphyria, and scar tissue and wounds.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A chemical compound comprising:
   at least one molecule of bacitracin having adjacent isoleucine and cysteine amino acid residues; and
   at least one selenium ion, each of said selenium ions being substituted for a sulfur atom in a sulfide bond between the adjacent isoleucine and cysteine amino acid residues in a corresponding bacitracin molecule.

2. A chemical compound as defined in claim 1 wherein said bacitracin is supported by a chemical support structure comprising at least one molecule of alpha-lactalbumin, said alpha-lactalbumin being linked to said bacitracin by a plurality of first organic linkages, each of said first organic linkages comprising a hydrocarbon chain having a length from about 8 to about 50 carbon atoms.

3. A chemical compound as defined in claim 2 wherein said first organic linkages are formed by reacting fatty acids with said alpha-lactalbumin and said bacitracin.

4. A chemical compound as defined in claim 1 wherein said bacitracin is supported by a chemical support structure comprising at least one molecule of alpha-lactalbumin, said alpha-lactalbumin being linked to said bacitracin by a plurality of first organic linkages, each of said first organic linkages comprising a hydrocarbon chain having a length from about 14 to about 20 carbon atoms.

5. A chemical compound as defined in claim 2 wherein the chemical support structure further comprises at least one molecule of beta-lactoglobulin, said beta-lactoglobulin being linked to said alpha-lactalbumin by a plurality of second organic linkages, each of said second organic linkages comprising a hydrocarbon chain having a length from about 8 to about 50 carbon atoms.

6. A chemical compound as defined in claim 5 wherein said second organic linkages are formed by reacting alcohols with said beta-lactoglobulin and said alpha-lactalbumin, said alcohols being selected from the group consisting of noncyclic aliphatic alcohols, steroid alcohols, and triterpenoid alcohols.

7. A chemical compound as defined in claim 2 wherein the chemical support structure further comprises at least one molecule of beta-lactoglobulin, said beta-lactoglobulin beig linked to said alpha-lactalbumin by a plurality of second organic linkages, each of said second organic linkages comprising a hydrocarbon chain having a length from about 14 to about 20 carbon atoms.

8. A chemical compound as defined in claim 5 wherein said beta-lactoglobulin is further linked to said alpha-lactalbumin by one or more third organic linkages, said third organic linkages being formed by reacting thioglycerol molecules with said beta-lactoglobulin and said alpha-lactalbumin.

9. A chemical compound as defined in claim 1 further comprising at least one zinc ion, each of said zinc ions being associated with at least one bacitracin molecule so as to form a salt therewith.

10. A chemical compound as defined in claim 1 further comprising at least one calcium ion, each of said calcium ions being associated with at least one bacitracin molecule so as to form a salt therewith.

11. A chemical compound as defined in claim 1 further comprising at least one magnesium ion, each of said magnesium ions being associated with at least one bacitracin molecule so as to form a salt therewith.

12. A chemical compound comprising:
   at least one molecule of beta-lactoglobulin;
   at least one molecule of alpha-lactalbumin, said alpha-lactalbumin being linked to said beta-lactoglobulin by a plurality of first organic linkages, each of said first organic linkages comprising a hydrocarbon chain having a length from about 8 to about 50 carbon atoms;
   at least one molecule of bacitracin having adjacent isoleucine and cysteine amino acid residues, said bacitracin being linked to said alpha-lactalbumin by a plurality of second organic linkages, each of said second organic linkages comprising a hydrocarbon chain having a length from about 8 to about 50 carbon atoms; and
   at least one selenium ion, each of said selenium ions being substituted for a sulfur atom in a sulfide bond between the adjacent isoleucine and cysteine amino acid residues in a corresponding bacitracin molecule.

13. A chemical compound as defined in claim 12 wherein each of said first organic linkages comprises a hydrocarbon chain having a length from about 14 to about 20 carbon atoms and wherein each of said second organic linkages comprises a hydrocarbon chain having a length from about 14 to about 20 carbon atoms.

14. A chemical compound as defined in claim 13 wherein said first organic linkages are formed by reacting alcohols with said alpha-lactalbumin and said beta-lactoglobulin, said alcohols being selected from the group consisting of noncyclic aliphatic alcohols, steroid alcohols, and triterpenoid alcohols.

15. A chemical compound as defined in claim 14 wherein said beta-lactoglobulin is further linked to said alpha-lactalbumin by one or more third organic linkages, said third organic linkages being formed by reacting thioglycerol molecules with said beta-lactoglobulin and said alpha-lactalbumin.

16. A chemical compound as defined in claim 13 wherein said second organic linkages are formed by reacting fatty acids with said bacitracin and said alpha-lactalbumin.

17. A chemical compound as defined in claim 12 further comprising at least one zinc ion, each of said zinc ions being associated with at least one bacitracin molecule so as to form a salt therewith.

18. A chemical compound as defined in claim 12 further comprising at least one calcium ion, each of said calcium ions being associated with at least one bacitracin molecule so as to form a salt therewith.

19. A chemical compound as defined in claim 12 further comprising at least one magnesium ion, each of said magnesium ions being associated with at least one bacitracin molecule so as to form a salt therewith.

20. A chemical compound as defined in claim 12 wherein each molecule of the compound comprises one molecule of beta-lactoglobulin, two molecules of alpha-lactalbumin, eight molecules of bacitracin, and eight selenium ions.

21. A chemical compound comprising:
   at least one molecule of beta-lactoglobulin;
   at least one molecule of alpha-lactalbumin; and
   a plurality of organic linkages linking said beta-lactoglobulin to said alpha-lactalbumin, each of said organic linkages comprising a hydrocarbon chain having a length from about 8 to about 50 carbon atoms.

22. A chemical compound as defined in claim 21 wherein said organic linkages are formed by reacting alcohols with said beta-lactoglobulin and said alpha-lactalbumin, said alcohols being selected from the group consisting of noncyclic aliphatic alcohols, steroid alcohols, and triterpenoid alcohols.

23. A chemical compound as defined in claim 22 wherein said beta-lactoglobulin is further linked to said alpha-lactalbumin by one or more second organic linkages, said second organic linkages being formed by reacting thioglycerol molecules with said beta-lactoglobulin and alpha-lactalbumin.

24. A chemical compound as defined in claim 21 wherein each of said organic linkages comprises a hydrocarbon chain having a length from about 14 to about 20 carbon atoms.

25. A chemical compound comprising:
   at least one molecule of beta-lactoglobulin; and
   a plurality of organic molecules attached to said beta-lactoglobulin, each of said organic molecules comprising a hydrocarbon chain having a length from about 8 to about 50 carbon atoms.

26. A chemical compound as defined in claim 25 wherein said organic molecules attached to said beta-lactoglobulin comprise alcohols which are reacted with said beta-lactoglobulin, said alcohols being selected from the group consisting of noncyclic aliphatic alcohols, steroid alcohols, and triterpenoid alcohols.

27. A chemical compound as defined in claim 25 wherein each of said organic molecules comprises a hydrocarbon chain having a length from about 14 to about 20 carbon atoms.

28. A chemical compound comprising:
   one molecule of beta-lactoglobulin;
   two molecules of alpha-lactalbumin;
   a plurality of first organic linkages linking said molecule of beta-lactoglobulin to said molecules of alpha-lactalbumin, said first organic linkages being formed by reacting alcohols with said molecule of beta-lactoglobulin and said molecules of alpha-lactalbumin, said alcohols being selected from the group consisting of noncyclic aliphatic alcohols, steroid alcohols, and triterpenoid alcohols, each of said alcohols comprising a hydrocarbon chain having a length from about 14 to about 20 carbon atoms;
   eight molecules of bacitracin, each of said bacitracin molecules having adjacent isoleucine and cysteine amino acid residues;
   a plurality of second organic linkages linking said molecules of alpha-lactalbumin to said molecules of bacitracin, said second organic linkages being formed by reacting fatty acids with said molecules of alpha-lactalbumin and said molecules of bacitracin, each of said fatty acids comprising a hydrocarbon chain having a length from about 14 to about 20 carbon atoms; and
   eight selenium ions, each of said selenium ions being substituted for a sulfur atom in a sulfide bond between the adjacent isoleucine and cysteine amino acid residues in a corresponding one of said bacitracin molecules.

29. A chemical compound as defined in claim 28 further comprising four zinc ions, each of said zinc ions being associated with two of said bacitracin molecules so as to form a salt therewith.

* * * * *